United States Patent
Lachia et al.

(10) Patent No.: US 9,131,688 B2
(45) Date of Patent: Sep. 15, 2015

(54) STRIGOLACTAM DERIVATIVES AS PLANT GROWTH REGULATING COMPOUNDS

(71) Applicant: Syngenta Participations AG, Basel (CH)

(72) Inventors: Mathilde Denise Lachia, Stein (CH); Alain De Mesmaeker, Stein (CH); Emmanuelle Villedieu-Percheron, Stein (CH); Hanno Christian Wolf, Stein (CH); Pierre Joseph Marcel Jung, Stein (CH); Frank Lanfermeijer, Enkhuizen (NL); Paul Van Den Wijngard, Eunkhuizen (NL); Claudio Screpanti, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/365,715

(22) PCT Filed: Dec. 14, 2012

(86) PCT No.: PCT/EP2012/075605
§ 371 (c)(1),
(2) Date: Jun. 16, 2014

(87) PCT Pub. No.: WO2013/092430
PCT Pub. Date: Jun. 27, 2013

(65) Prior Publication Data
US 2014/0336052 A1 Nov. 13, 2014

(30) Foreign Application Priority Data

Dec. 19, 2011 (GB) .................................. 1121904.5
Mar. 8, 2012 (GB) .................................. 1204149.7

(51) Int. Cl.
*C07D 209/70* (2006.01)
*C07D 401/04* (2006.01)
*C07D 405/12* (2006.01)
*C07D 405/14* (2006.01)
*C07D 417/04* (2006.01)
*C07D 417/14* (2006.01)
*A01N 43/38* (2006.01)
*A01N 43/30* (2006.01)
*A01N 43/90* (2006.01)

(52) U.S. Cl.
CPC .............. *A01N 43/38* (2013.01); *C07D 209/70* (2013.01); *C07D 405/12* (2013.01)

(58) Field of Classification Search
USPC .......................................................... 548/450
See application file for complete search history.

(56) References Cited

FOREIGN PATENT DOCUMENTS

| WO | 2009138655 | 11/2009 |
|----|------------|---------|
| WO | 2012080115 | 6/2012 |

OTHER PUBLICATIONS

Johnsson et al., "The preparation of synthetic analogues of strigol," Journal of the Chemical Society, Perkin Transactions 1, Chemical Society, Letchworth; GB, Jan. 1, 1981, No. 6, pp. 1734-1743.
International Search Report dated Apr. 15, 2013 for International Patent Application No. PCT/EP2012/075605.

*Primary Examiner* — Nyeemah A Grazier
(74) *Attorney, Agent, or Firm* — R. Kody Jones

(57) ABSTRACT

The present invention relates to novel strigolactam derivatives of formula (I), to processes and intermediates for preparing them, to plant growth regulator compositions comprising them and to methods of using them for controlling the growth of plants and/or promoting the germination of seeds.

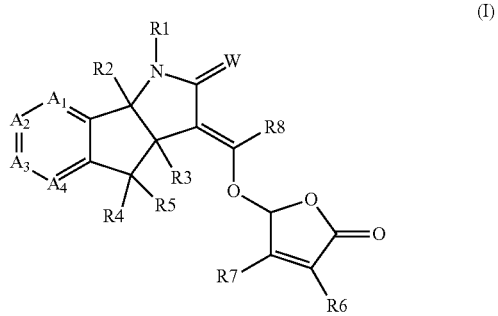

(I)

16 Claims, No Drawings

STRIGOLACTAM DERIVATIVES AS PLANT GROWTH REGULATING COMPOUNDS

RELATED APPLICATION INFORMATION

This application is a 371 of International Application No. PCT/EP2012/075605, filed 14 Dec. 2012, which claims priority to GB Application No. 1121904.5, filed 19 Dec. 2011, and GB Application No. 1204149.7 filed 8 Mar. 2012, the contents of which are incorporated herein by reference herein.

The present invention relates to novel strigolactam derivatives, to processes and intermediates for preparing them, to plant growth regulator compositions comprising them and to methods of using them for controlling the growth of plants and/or promoting the germination of seeds.

Strigolactone derivatives are phytohormones with plant growth regulation and seed germination properties; they have been described, for example, in WO2009/138655, WO2010/125065, WO05/077177, WO06/098626, and Annual Review of Phytopathology (2010), 48 p. 93-117. Strigolactone derivatives, like the synthetic analogue GR24, are known to have effect on the germination of parasitic weeds, such as *Orobanche* species. It is well established in the art that testing for germination of *Orobanche* seeds is a useful test to identify strigolactone analogues (for example, see Plant and Cell Physiology (2010), 51(7) p. 1095; and Organic & Biomolecular Chemistry (2009), 7(17), p. 3413).

It has now surprisingly been found that certain strigolactam derivatives have properties analogous to strigolactone. These were also found to have crop enhancement properties.

According to the present invention, there is provided a compound of Formula (I)

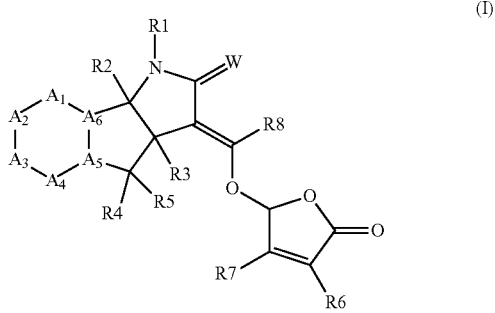

(I)

wherein
W is O or S;
R2 and R3 are independently hydrogen, or $C_1$-$C_3$ alkyl;
R4 and R5 are independently hydrogen, halogen, nitro, cyano, $C_1$-$C_3$ alkyl, $C_1$-$C_3$ haloalkyl, $C_1$-$C_3$ alkoxy, hydroxyl, —OC(O)R9, amine, N—$C_1$-$C_3$ alkyl amine, or N,N-di-$C_1$-$C_3$ alkyl amine;
R9 is hydrogen, $C_1$-$C_6$ alkyl, $C_1$-$C_6$ alkoxy, or $C_1$-$C_6$ haloalkyl;
R6 and R7 are independently hydrogen, $C_1$-$C_3$ alkyl, hydroxyl, halogen or $C_1$-$C_3$ alkoxy;
R8 is hydrogen, nitro, cyano, $C_1$-$C_6$ alkyl, $C_1$-$C_6$ haloalkyl, halogen, $C_1$-$C_8$ alkylthio, $C_1$-$C_8$ haloalkylthio, $C_1$-$C_8$ alkylsulfinyl, N—$C_1$-$C_6$ alkyl amine, N,N-di-$C_1$-$C_6$ alkyl amine, $C_1$-$C_8$ haloalkylsulfinyl, $C_1$-$C_8$ alkylsulfonyl, or $C_1$-$C_8$ haloalkylsulfonyl;
R1 is hydrogen, $C_1$-$C_6$ alkoxy, hydroxyl, amine, N—$C_1$-$C_6$ alkyl amine, N,N-di-$C_1$-$C_6$ alkyl amine, $C_1$-$C_6$ alkyl optionally substituted by one to five R10, $C_1$-$C_8$ alkylcarbonyl, $C_1$-$C_8$ alkoxycarbonyl, aryl, optionally substituted by one to five R10, heteroaryl, optionally substituted by one to five R10, heterocyclyl, optionally substituted by one to five R10, or benzyl optionally substituted by one to five R10;
R10 is hydrogen, cyano, nitro, halogen, $C_1$-$C_6$ alkyl, $C_1$-$C_6$ alkoxy, $C_1$-$C_6$ haloalkyl, $C_2$-$C_6$ alkenyl, or $C_2$-$C_6$ alkynyl;
$A_1$, $A_2$, and $A_3$ are each independently C-Xn, C-(Xn)C-(Xn), a heteroatom selected from O, S and N, wherein each X may be the same or different, or a bond;
$A_4$ is C-Xn, or a heteroatom selected from O, S and N, wherein each X may be the same or different;
$A_5$, and $A_6$ are each independently C-X, nitrogen, or C linked by a double bond, wherein each X may be the same or different;
$A_1$ and $A_2$, $A_2$ and $A_3$, $A_3$ and $A_4$, $A_4$ and $A_5$, $A_5$ and $A_6$, $A_6$ and $A_1$ are linked independently of each other by a single or double bond provided that $A_1$ to $A_6$ is not an aromatic ring;
n is 1 or 2;
X is hydrogen, halogen, cyano, amine, nitro, hydroxyl, —OC(O)R9, $C_1$-$C_6$ alkoxy, $C_1$-$C_6$ alkyl, $C_1$-$C_6$ haloalkyl, $C_1$-$C_6$ hydroxyalkyl; $C_2$-$C_8$ alkenyl optionally substituted by one to five R11, $C_2$-$C_8$ alkynyl optionally substituted by one to five R11, $C_3$-$C_7$ cycloalkyl, $C_3$-$C_{10}$ cycloalkyl substituted by one to five R11, $C_1$-$C_8$alkylcarbonyl, $C_1$-$C_8$ alkoxycarbonyl, N—$C_1$-$C_6$ alkyl aminocarbonyl, N,N-di-$C_1$-$C_6$ alkyl aminocarbonyl, aryl optionally substituted by one to five R11, or heterocyclic optionally substituted by one to five R11; and
R11 is halogen, nitro, cyano, hydroxyl, —OC(O)R9, $C_1$-$C_6$ alkoxy, $C_1$-$C_6$ alkyl, $C_1$-$C_6$ haloalkyl;
or salts or N-oxides thereof.

The compounds of Formula (I) may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of Formula (I).

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$ to $C_6$ alkyl groups, more preferably $C_1$-$C_4$ and most preferably $C_1$-$C_3$ alkyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$.

Hydroxyalkyl groups are alkyl groups which are substituted with one or more hydroxyl group and are, for example, —$CH_2OH$, —$CH_2CH_2OH$ or —$CH(OH)CH_3$.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

Unless otherwise indicated, alkenyl and alkynyl, on their own or as part of another substituent, may be straight or branched chain and may preferably contain 2 to 6 carbon atoms, preferably 2 to 4, more preferably 2 to 3, and where appropriate, may be in either the (E)- or (Z)-configuration. Examples include vinyl, allyl and propargyl.

Unless otherwise indicated, cycloalkyl may be mono- or bi-cyclic, may be optionally substituted by one or more $C_1$-$C_6$alkyl groups, and preferably contain 3 to 7 carbon atoms, more preferably 3 to 6 carbon atoms. Examples of cycloalkyl include cyclopropyl, 1-methylcyclopropyl, 2-methylcyclopropyl, cyclobutyl, cyclopentyl and cyclohexyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine.

The term "heterocyclyl" is defined to include heteroaryl, saturated analogs, and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzo-furanyl, piperidinyl, 1,3-dioxolanyl, 1,3-dioxanyl, 4,5-dihydro-isoxazolyl, tetrahydrofuranyl and morpholinyl. In addition, the term "heterocyclyl" is defined to include "heterocycloalkyl" defined to be a non-aromatic monocyclic or polycyclic ring comprising carbon and hydrogen atoms and at least one heteroatom, preferably, 1 to 4 heteroatoms selected from nitrogen, oxygen, and sulfur such as oxirane or thietane.

Preferred values of W, R1, R2, R3, R4, R5, R6, R7, R8, R10, $A_1$, $A_2$, $A_3$, $A_4$, $A_5$, $A_6$ and X are, in any combination, as set out below.

W is preferably oxygen.

R2 is preferably hydrogen, methyl, or ethyl; most preferably R2 is hydrogen.

R3 is preferably hydrogen, methyl, or ethyl; most preferably R3 is hydrogen.

R4 is preferably hydrogen, hydroxyl, methyl, or ethyl; most preferably R4 is hydrogen or hydroxyl.

R5 is preferably hydrogen, hydroxyl, methyl, or ethyl; most preferably R5 is hydrogen or hydroxyl.

R6 is preferably hydrogen, methyl, or ethyl; most preferably R6 is methyl.

R7 is preferably hydrogen, methyl, methoxy, chlorine or ethyl; most preferably R7 is hydrogen.

R8 is preferably hydrogen, methyl, or ethyl; most preferably R8 is hydrogen.

R1 is preferably hydrogen, $C_1$-$C_6$ alkoxy, $C_1$-$C_6$ alkyl optionally substituted by one to five R10, $C_1$-$C_8$ alkylcarbonyl, $C_1$-$C_8$ alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10. More preferably R1 is hydrogen, $C_1$-$C_6$ alkoxy, $C_1$-$C_6$ alkyl substituted or not by one to five R10, $C_1$-$C_8$ alkylcarbonyl, $C_1$-$C_8$ alkoxycarbonyl, aryl, aryl substituted by one to five R10, benzyl, or benzyl substituted by one to five R10. Most preferably R1 is hydrogen, methyl, ethyl, phenyl, benzyl, acetate, or methoxycarbonyl.

R10 is independently hydrogen, cyano, nitro, halogen, $C_1$-$C_6$ alkyl, $C_1$-$C_6$ alkoxy, $C_1$-$C_6$ haloalkyl; most preferably R10 is hydrogen, cyano, nitro, chloride, bromine, fluorine, methyl, methoxy, or trifluoromethyl.

Preferably $A_1$, $A_2$, $A_3$ and $A_4$ are C-Xn, wherein n is 1 or 2.

Preferably $A_5$ and $A_6$ are independently C-X, or C linked by a double bond; most preferably $A_5$ and $A_6$ are C linked by a double bond.

In one embodiment, $A_1$ to $A_6$ is a carbonyl ring. In a further embodiment, $A_1$ to $A_6$ is a 6-membered carbonyl ring.

Preferably X is hydrogen, methyl, ethyl, fluoro, hydroxyl, methylhydroxyl, methoxy, or methylacetate.

In a preferred embodiment the compound is of Formula (II).

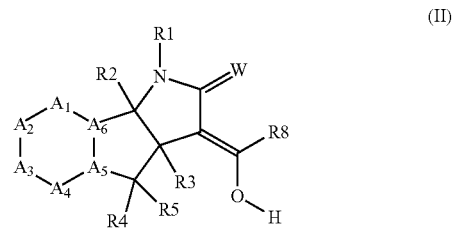

(II)

wherein

W is O or S;

R2 and R3 are independently hydrogen, or $C_1$-$C_3$ alkyl;

R4 and R5 are independently hydrogen, halogen, nitro, cyano, $C_1$-$C_3$ alkyl, $C_1$-$C_3$ haloalkyl, $C_1$-$C_3$ alkoxy, hydroxyl, —OC(O)R9, amine, N—$C_1$-$C_3$ alkyl amine, or N,N-di-$C_1$-$C_3$ alkyl amine;

R9 is hydrogen, $C_1$-$C_6$ alkyl, $C_1$-$C_6$ alkoxy, or $C_1$-$C_6$ haloalkyl;

R8 is hydrogen, nitro, cyano, $C_1$-$C_6$ alkyl, $C_1$-$C_6$ haloalkyl, halogen. $C_1$-$C_8$ alkylthio, $C_1$-$C_8$ haloalkylthio, $C_1$-$C_8$ alkylsulfinyl, N—$C_1$-$C_6$ alkyl amine, N,N-di-$C_1$-$C_6$ alkyl amine, $C_1$-$C_8$ haloalkylsulfinyl, $C_1$-$C_8$ alkylsulfonyl, or $C_1$-$C_8$ haloalkylsulfonyl;

R1 is hydrogen, $C_1$-$C_6$ alkoxy, hydroxyl, amine, N—$C_1$-$C_6$ alkyl amine, N,N-di-$C_1$-$C_6$ alkyl amine, $C_1$-$C_6$ alkyl optionally substituted by one to five R10, $C_1$-$C_8$ alkylcarbonyl, $C_1$-$C_8$ alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;

R10 is hydrogen, cyano, nitro, halogen, $C_1$-$C_6$ alkyl, $C_1$-$C_6$ alkoxy, $C_1$-$C_6$ haloalkyl, $C_2$-$C_6$ alkenyl, or $C_2$-$C_6$ alkynyl;

$A_1$, $A_2$, and $A_3$ are each independently C-Xn, C-(Xn)C-(Xn), a heteroatom selected from O, S and N, wherein each X may be the same or different, or a bond;

$A_4$ is C-Xn, or a heteroatom selected from O, S and N, wherein each X may be the same or different;

$A_5$, and $A_6$ are each independently C-X, nitrogen, or C linked by a double bond, wherein each X may be the same or different;

$A_1$ and $A_2$, $A_2$ and $A_3$, $A_3$ and $A_4$, $A_4$ and $A_5$, $A_5$ and $A_6$, $A_6$ and $A_1$ are linked independently of each other by a single or double bond provided that $A_1$ to $A_6$ is not an aromatic ring;

n is 1 or 2;

X is hydrogen, halogen, cyano, amine, nitro, hydroxyl, —OC(O)R9, $C_1$-$C_6$ alkoxy, $C_1$-$C_6$ alkyl, $C_1$-$C_6$ haloalkyl, $C_1$-$C_6$ hydroxyalkyl; $C_2$-$C_8$ alkenyl optionally substituted by one to five R11, $C_2$-$C_8$ alkynyl optionally substituted by one to five R11, $C_3$-$C_7$ cycloalkyl, $C_3$-$C_{10}$ cycloalkyl substituted by one to five R11, $C_1$-$C_8$alkylcarbonyl, $C_1$-$C_8$ alkoxycarbonyl, N—$C_1$-$C_6$ alkyl aminocarbonyl, N,N-di-$C_1$-$C_6$ alkyl aminocarbonyl, aryl optionally substituted by one to five R11, or heterocyclic optionally substituted by one to five R11; and R11 is halogen, nitro, cyano, hydroxyl, —OC(O)R9, $C_1$-$C_6$ alkoxy, $C_1$-$C_6$ alkyl, $C_1$-$C_6$ haloalkyl;

or salts or N-oxides thereof.

The preferences for $A_1, A_2, A_3, A_4, A_5, A_6$, R1, R2, R3, R4, R5, R8 and W are the same as the preferences set out for the corresponding substituents of the compounds of the Formula (I).

Table 1 below includes examples of compounds of Formula (I) wherein W is O, R2 is H, R3 is H, R6 is methyl, R7 is H, R8 is H and $A_1, A_2, A_3, A_4, A_5, A_6$, R1, R4 and R5 are as defined.

TABLE 1

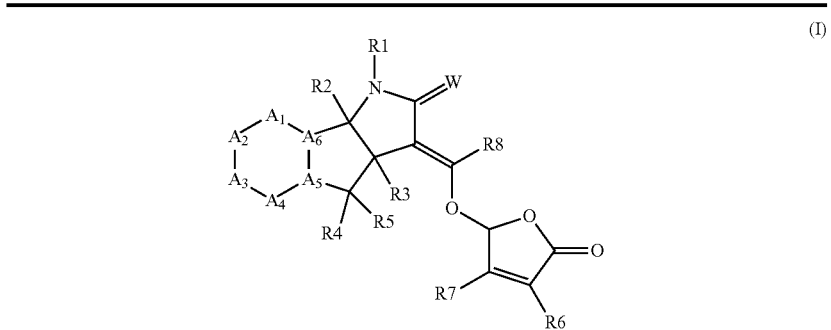

(I)

| Compound | R1 | R4 | R5 | $A_1$ | $A_2$ | $A_3$ | $A_4$ | $A_5$ | $A_6$ |
|---|---|---|---|---|---|---|---|---|---|
| 1.00 | H | H | H | $CH_2$ | $CH_2$ | $CH_2$ | $CH_2$ | C=C | |
| 1.01 | H | H | H | $CH(CH_3)$ | $CH_2$ | $CH_2$ | $CH_2$ | C=C | |
| 1.02 | H | H | H | $C(CH_3)_2$ | $CH_2$ | $CH_2$ | $CH_2$ | C=C | |
| 1.03 | H | H | H | $C(CH_3)(CH_2OH)$ | $CH_2$ | $CH_2$ | $CH_2$ | C=C | |
| 1.04 | H | H | H | $CH_2$ | $CH_2$ | $CH_2$ | $CH(OH)$ | C=C | |
| 1.05 | H | H | H | $CH(CH_3)$ | $CH_2$ | $CH_2$ | $CH(OH)$ | C=C | |
| 1.06 | H | H | H | $C(CH_3)_2$ | $CH_2$ | $CH_2$ | $CH(OH)$ | C=C | |
| 1.07 | H | H | H | $C(CH_3)(CH_2OH)$ | $CH_2$ | $CH_2$ | $CH(OH)$ | C=C | |
| 1.08 | H | H | H | $CH_2$ | $CH_2$ | $CH_2$ | $CH(OC(O)CH_3)$ | C=C | |
| 1.09 | H | H | H | $CH(CH_3)$ | $CH_2$ | $CH_2$ | $CH(OC(O)CH_3)$ | C=C | |
| 1.10 | H | H | H | $C(CH_3)_2$ | $CH_2$ | $CH_2$ | $CH(OC(O)CH_3)$ | C=C | |
| 1.11 | H | H | H | $C(CH_3)(CH_2OH)$ | $CH_2$ | $CH_2$ | $CH(OC(O)CH_3)$ | C=C | |
| 1.12 | H | H | H | $CH_2$ | $CH_2$ | $CH_2$ | $CH(CH_3)$ | C=C | |
| 1.13 | H | H | H | $CH(CH_3)$ | $CH_2$ | $CH_2$ | $CH(CH_3)$ | C=C | |
| 1.14 | H | H | H | $C(CH_3)_2$ | $CH_2$ | $CH_2$ | $CH(CH_3)$ | C=C | |
| 1.15 | H | H | H | $C(CH_3)(CH_2OH)$ | $CH_2$ | $CH_2$ | $CH(CH_3)$ | C=C | |
| 1.16 | $CH_3$ | H | H | $CH_2$ | $CH_2$ | $CH_2$ | $CH_2$ | C=C | |
| 1.17 | $CH_3$ | H | H | $CH(CH_3)$ | $CH_2$ | $CH_2$ | $CH_2$ | C=C | |
| 1.18 | $CH_3$ | H | H | $C(CH_3)_2$ | $CH_2$ | $CH_2$ | $CH_2$ | C=C | |
| 1.19 | $CH_3$ | H | H | $C(CH_3)(CH_2OH)$ | $CH_2$ | $CH_2$ | $CH_2$ | C=C | |
| 1.20 | $CH_3$ | H | H | $CH_2$ | $CH_2$ | $CH_2$ | $CH(OH)$ | C=C | |
| 1.21 | $CH_3$ | H | H | $CH(CH_3)$ | $CH_2$ | $CH_2$ | $CH(OH)$ | C=C | |
| 1.22 | $CH_3$ | H | H | $C(CH_3)_2$ | $CH_2$ | $CH_2$ | $CH(OH)$ | C=C | |
| 1.23 | $CH_3$ | H | H | $C(CH_3)(CH_2OH)$ | $CH_2$ | $CH_2$ | $CH(OH)$ | C=C | |
| 1.24 | $CH_3$ | H | H | $CH_2$ | $CH_2$ | $CH_2$ | $CH(OC(O)CH_3)$ | C=C | |
| 1.25 | $CH_3$ | H | H | $CH(CH_3)$ | $CH_2$ | $CH_2$ | $CH(OC(O)CH_3)$ | C=C | |
| 1.26 | $CH_3$ | H | H | $C(CH_3)_2$ | $CH_2$ | $CH_2$ | $CH(OC(O)CH_3)$ | C=C | |
| 1.27 | $CH_3$ | H | H | $C(CH_3)(CH_2OH)$ | $CH_2$ | $CH_2$ | $CH(OC(O)CH_3)$ | C=C | |
| 1.28 | $CH_3$ | H | H | $CH_2$ | $CH_2$ | $CH_2$ | $CH(CH_3)$ | C=C | |
| 1.29 | $CH_3$ | H | H | $CH(CH_3)$ | $CH_2$ | $CH_2$ | $CH(CH_3)$ | C=C | |
| 1.30 | $CH_3$ | H | H | $C(CH_3)_2$ | $CH_2$ | $CH_2$ | $CH(CH_3)$ | C=C | |
| 1.31 | $CH_3$ | H | H | $C(CH_3)(CH_2OH)$ | $CH_2$ | $CH_2$ | $CH(CH_3)$ | C=C | |
| 1.32 | H | OH | H | $CH_2$ | $CH_2$ | $CH_2$ | $CH_2$ | C=C | |
| 1.33 | H | OH | H | $CH(CH_3)$ | $CH_2$ | $CH_2$ | $CH_2$ | C=C | |
| 1.34 | H | OH | H | $C(CH_3)_2$ | $CH_2$ | $CH_2$ | $CH_2$ | C=C | |
| 1.35 | H | OH | H | $C(CH_3)(CH_2OH)$ | $CH_2$ | $CH_2$ | $CH_2$ | C=C | |
| 1.36 | H | OH | H | $CH_2$ | $CH_2$ | $CH_2$ | $CH(OH)$ | C=C | |
| 1.37 | H | OH | H | $CH(CH_3)$ | $CH_2$ | $CH_2$ | $CH(OH)$ | C=C | |
| 1.38 | H | OH | H | $C(CH_3)_2$ | $CH_2$ | $CH_2$ | $CH(OH)$ | C=C | |
| 1.39 | H | OH | H | $C(CH_3)(CH_2OH)$ | $CH_2$ | $CH_2$ | $CH(OH)$ | C=C | |
| 1.40 | H | OH | H | $CH_2$ | $CH_2$ | $CH_2$ | $CH(OC(O)CH_3)$ | C=C | |
| 1.41 | H | OH | H | $CH(CH_3)$ | $CH_2$ | $CH_2$ | $CH(OC(O)CH_3)$ | C=C | |
| 1.42 | H | OH | H | $C(CH_3)_2$ | $CH_2$ | $CH_2$ | $CH(OC(O)CH_3)$ | C=C | |
| 1.43 | H | OH | H | $C(CH_3)(CH_2OH)$ | $CH_2$ | $CH_2$ | $CH(OC(O)CH_3)$ | C=C | |
| 1.44 | H | OH | H | $CH_2$ | $CH_2$ | $CH_2$ | $CH(CH_3)$ | C=C | |
| 1.45 | H | OH | H | $CH(CH_3)$ | $CH_2$ | $CH_2$ | $CH(CH_3)$ | C=C | |
| 1.46 | H | OH | H | $C(CH_3)_2$ | $CH_2$ | $CH_2$ | $CH(CH_3)$ | C=C | |
| 1.47 | H | OH | H | $C(CH_3)(CH_2OH)$ | $CH_2$ | $CH_2$ | $CH(CH_3)$ | C=C | |
| 1.48 | $CH_3$ | OH | H | $CH_2$ | $CH_2$ | $CH_2$ | $CH_2$ | C=C | |
| 1.49 | $CH_3$ | OH | H | $CH(CH_3)$ | $CH_2$ | $CH_2$ | $CH_2$ | C=C | |
| 1.50 | $CH_3$ | OH | H | $C(CH_3)_2$ | $CH_2$ | $CH_2$ | $CH_2$ | C=C | |
| 1.51 | $CH_3$ | OH | H | $C(CH_3)(CH_2OH)$ | $CH_2$ | $CH_2$ | $CH_2$ | C=C | |
| 1.52 | $CH_3$ | OH | H | $CH_2$ | $CH_2$ | $CH_2$ | $CH(OH)$ | C=C | |
| 1.53 | $CH_3$ | OH | H | $CH(CH_3)$ | $CH_2$ | $CH_2$ | $CH(OH)$ | C=C | |
| 1.54 | $CH_3$ | OH | H | $C(CH_3)_2$ | $CH_2$ | $CH_2$ | $CH(OH)$ | C=C | |
| 1.55 | $CH_3$ | OH | H | $C(CH_3)(CH_2OH)$ | $CH_2$ | $CH_2$ | $CH(OH)$ | C=C | |

TABLE 1-continued

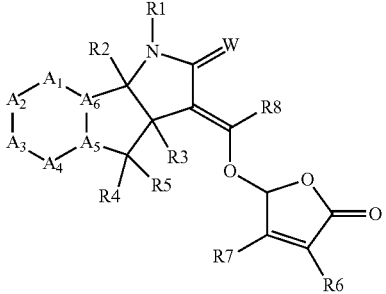

(I)

| Compound | R1 | R4 | R5 | $A_1$ | $A_2$ | $A_3$ | $A_4$ | $A_5$ | $A_6$ |
|---|---|---|---|---|---|---|---|---|---|
| 1.56 | $CH_3$ | OH | H | $CH_2$ | $CH_2$ | $CH_2$ | $CH(OC(O)CH_3)$ | C=C | |
| 1.57 | $CH_3$ | OH | H | $CH(CH_3)$ | $CH_2$ | $CH_2$ | $CH(OC(O)CH_3)$ | C=C | |
| 1.58 | $CH_3$ | OH | H | $C(CH_3)_2$ | $CH_2$ | $CH_2$ | $CH(OC(O)CH_3)$ | C=C | |
| 1.59 | $CH_3$ | OH | H | $C(CH_3)(CH_2OH)$ | $CH_2$ | $CH_2$ | $CH(OC(O)CH_3)$ | C=C | |
| 1.60 | $CH_3$ | OH | H | $CH_2$ | $CH_2$ | $CH_2$ | $CH(CH_3)$ | C=C | |
| 1.61 | $CH_3$ | OH | H | $CH(CH_3)$ | $CH_2$ | $CH_2$ | $CH(CH_3)$ | C=C | |
| 1.62 | $CH_3$ | OH | H | $C(CH_3)_2$ | $CH_2$ | $CH_2$ | $CH(CH_3)$ | C=C | |
| 1.63 | $CH_3$ | OH | H | $C(CH_3)(CH_2OH)$ | $CH_2$ | $CH_2$ | $CH(CH_3)$ | C=C | |
| 1.64 | H | $OC(O)CH_3$ | H | $CH_2$ | $CH_2$ | $CH_2$ | $CH_2$ | C=C | |
| 1.65 | H | $OC(O)CH_3$ | H | $CH(CH_3)$ | $CH_2$ | $CH_2$ | $CH_2$ | C=C | |
| 1.66 | H | $OC(O)CH_3$ | H | $C(CH_3)_2$ | $CH_2$ | $CH_2$ | $CH_2$ | C=C | |
| 1.67 | H | $OC(O)CH_3$ | H | $C(CH_3)(CH_2OH)$ | $CH_2$ | $CH_2$ | $CH_2$ | C=C | |
| 1.68 | H | $OC(O)CH_3$ | H | $CH_2$ | $CH_2$ | $CH_2$ | $CH(OH)$ | C=C | |
| 1.69 | H | $OC(O)CH_3$ | H | $CH(CH_3)$ | $CH_2$ | $CH_2$ | $CH(OH)$ | C=C | |
| 1.70 | H | $OC(O)CH_3$ | H | $C(CH_3)_2$ | $CH_2$ | $CH_2$ | $CH(OH)$ | C=C | |
| 1.71 | H | $OC(O)CH_3$ | H | $C(CH_3)(CH_2OH)$ | $CH_2$ | $CH_2$ | $CH(OH)$ | C=C | |
| 1.72 | H | $OC(O)CH_3$ | H | $CH_2$ | $CH_2$ | $CH_2$ | $CH(OC(O)CH_3)$ | C=C | |
| 1.73 | H | $OC(O)CH_3$ | H | $CH(CH_3)$ | $CH_2$ | $CH_2$ | $CH(OC(O)CH_3)$ | C=C | |
| 1.74 | H | $OC(O)CH_3$ | H | $C(CH_3)_2$ | $CH_2$ | $CH_2$ | $CH(OC(O)CH_3)$ | C=C | |
| 1.75 | H | $OC(O)CH_3$ | H | $C(CH_3)(CH_2OH)$ | $CH_2$ | $CH_2$ | $CH(OC(O)CH_3)$ | C=C | |
| 1.76 | H | $OC(O)CH_3$ | H | $CH_2$ | $CH_2$ | $CH_2$ | $CH(CH_3)$ | C=C | |
| 1.77 | H | $OC(O)CH_3$ | H | $CH(CH_3)$ | $CH_2$ | $CH_2$ | $CH(CH_3)$ | C=C | |
| 1.78 | H | $OC(O)CH_3$ | H | $C(CH_3)_2$ | $CH_2$ | $CH_2$ | $CH(CH_3)$ | C=C | |
| 1.79 | H | $OC(O)CH_3$ | H | $C(CH_3)(CH_2OH)$ | $CH_2$ | $CH_2$ | $CH(CH_3)$ | C=C | |
| 1.80 | $CH_3$ | $OC(O)CH_3$ | H | $CH_2$ | $CH_2$ | $CH_2$ | $CH_2$ | C=C | |
| 1.81 | $CH_3$ | $OC(O)CH_3$ | H | $CH(CH_3)$ | $CH_2$ | $CH_2$ | $CH_2$ | C=C | |
| 1.82 | $CH_3$ | $OC(O)CH_3$ | H | $C(CH_3)_2$ | $CH_2$ | $CH_2$ | $CH_2$ | C=C | |
| 1.83 | $CH_3$ | $OC(O)CH_3$ | H | $C(CH_3)(CH_2OH)$ | $CH_2$ | rr$_2$ | $CH_2$ | C=C | |
| 1.84 | $CH_3$ | $OC(O)CH_3$ | H | $CH_2$ | $CH_2$ | $CH_2$ | $CH(OH)$ | C=C | |
| 1.85 | $CH_3$ | $OC(O)CH_3$ | H | $CH(CH_3)$ | $CH_2$ | $CH_2$ | $CH(OH)$ | C=C | |
| 1.86 | $CH_3$ | $OC(O)CH_3$ | H | $C(CH_3)_2$ | $CH_2$ | $CH_2$ | $CH(OH)$ | C=C | |
| 1.87 | $CH_3$ | $OC(O)CH_3$ | H | $C(CH_3)(CH_2OH)$ | $CH_2$ | $CH_2$ | $CH(OH)$ | C=C | |
| 1.88 | $CH_3$ | $OC(O)CH_3$ | H | $CH_2$ | $CH_2$ | $CH_2$ | $CH(OC(O)CH_3)$ | C=C | |
| 1.89 | $CH_3$ | $OC(O)CH_3$ | H | $CH(CH_3)$ | $CH_2$ | $CH_2$ | $CH(OC(O)CH_3)$ | C=C | |
| 1.90 | $CH_3$ | $OC(O)CH_3$ | H | $C(CH_3)_2$ | $CH_2$ | $CH_2$ | $CH(OC(O)CH_3)$ | C=C | |
| 1.91 | $CH_3$ | $OC(O)CH_3$ | H | $C(CH_3)(CH_2OH)$ | $CH_2$ | $CH_2$ | $CH(OC(O)CH_3)$ | C=C | |
| 1.92 | $CH_3$ | $OC(O)CH_3$ | H | $CH_2$ | $CH_2$ | $CH_2$ | $CH(CH_3)$ | C=C | |
| 1.93 | $CH_3$ | $OC(O)CH_3$ | H | $CH(CH_3)$ | $CH_2$ | $CH_2$ | $CH(CH_3)$ | C=C | |
| 1.94 | $CH_3$ | $OC(O)CH_3$ | H | $C(CH_3)_2$ | $CH_2$ | $CH_2$ | $CH(CH_3)$ | C=C | |
| 1.95 | $CH_3$ | $OC(O)CH_3$ | H | $C(CH_3)(CH_2OH)$ | $CH_2$ | $CH_2$ | $CH(CH_3)$ | C=C | |

Tables 2 below includes examples of compounds of Formula (II) wherein W is O, R2 is H, R3 is H, R8 is H and $A_1$, $A_2$, $A_3$, $A_4$, R1, R4 and R5 are as defined.

TABLE 2

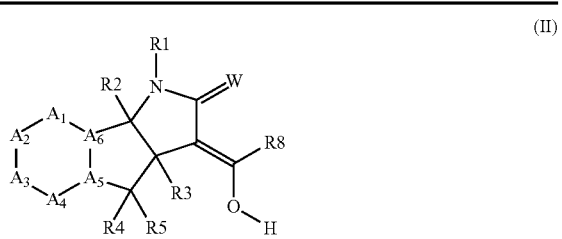

(II)

| Compound | R1 | R4 | R5 | $A_1$ | $A_2$ | $A_3$ | $A_4$ | $A_5$ | $A_6$ |
|---|---|---|---|---|---|---|---|---|---|
| 2.00 | H | H | H | $CH_2$ | $CH_2$ | $CH_2$ | $CH_2$ | C=C | |
| 2.01 | H | H | H | $CH(CH_3)$ | $CH_2$ | $CH_2$ | $CH_2$ | C=C | |
| 2.02 | H | H | H | $C(CH_3)_2$ | $CH_2$ | $CH_2$ | $CH_2$ | C=C | |
| 2.03 | H | H | H | $C(CH_3)(CH_2OH)$ | $CH_2$ | $CH_2$ | $CH_2$ | C=C | |
| 2.04 | H | H | H | $CH_2$ | $CH_2$ | $CH_2$ | $CH(OH)$ | C=C | |
| 2.05 | H | H | H | $CH(CH_3)$ | $CH_2$ | $CH_2$ | $CH(OH)$ | C=C | |
| 2.06 | H | H | H | $C(CH_3)_2$ | $CH_2$ | $CH_2$ | $CH(OH)$ | C=C | |
| 2.07 | H | H | H | $C(CH_3)(CH_2OH)$ | $CH_2$ | $CH_2$ | $CH(OH)$ | C=C | |
| 2.08 | H | H | H | $CH_2$ | $CH_2$ | $CH_2$ | $CH(OC(O)CH_3)$ | C=C | |
| 2.09 | H | H | H | $CH(CH_3)$ | $CH_2$ | $CH_2$ | $CH(OC(O)CH_3)$ | C=C | |
| 2.10 | H | H | H | $C(CH_3)_2$ | $CH_2$ | $CH_2$ | $CH(OC(O)CH_3)$ | C=C | |
| 2.11 | H | H | H | $C(CH_3)(CH_2OH)$ | $CH_2$ | $CH_2$ | $CH(OC(O)CH_3)$ | C=C | |
| 2.12 | H | H | H | $CH_2$ | $CH_2$ | $CH_2$ | $CH(CH_3)$ | C=C | |
| 2.13 | H | H | H | $CH(CH_3)$ | $CH_2$ | $CH_2$ | $CH(CH_3)$ | C=C | |
| 2.14 | H | H | H | $C(CH_3)_2$ | $CH_2$ | $CH_2$ | $CH(CH_3)$ | C=C | |
| 2.15 | H | H | H | $C(CH_3)(CH_2OH)$ | $CH_2$ | $CH_2$ | $CH(CH_3)$ | C=C | |
| 2.16 | CH3 | H | H | $CH_2$ | $CH_2$ | $CH_2$ | $CH_2$ | C=C | |
| 2.17 | CH3 | H | H | $CH(CH_3)$ | $CH_2$ | $CH_2$ | $CH_2$ | C=C | |
| 2.18 | CH3 | H | H | $C(CH_3)_2$ | $CH_2$ | $CH_2$ | $CH_2$ | C=C | |
| 2.19 | CH3 | H | H | $C(CH_3)(CH_2OH)$ | $CH_2$ | $CH_2$ | $CH_2$ | C=C | |
| 2.20 | CH3 | H | H | $CH_2$ | $CH_2$ | $CH_2$ | $CH(OH)$ | C=C | |
| 2.21 | CH3 | H | H | $CH(CH_3)$ | $CH_2$ | $CH_2$ | $CH(OH)$ | C=C | |
| 2.22 | CH3 | H | H | $C(CH_3)_2$ | $CH_2$ | $CH_2$ | $CH(OH)$ | C=C | |
| 2.23 | CH3 | H | H | $C(CH_3)(CH_2OH)$ | $CH_2$ | $CH_2$ | $CH(OH)$ | C=C | |
| 2.24 | CH3 | H | H | $CH_2$ | $CH_2$ | $CH_2$ | $CH(OC(O)CH_3)$ | C=C | |
| 2.25 | CH3 | H | H | $CH(CH_3)$ | $CH_2$ | $CH_2$ | $CH(OC(O)CH_3)$ | C=C | |
| 2.26 | CH3 | H | H | $C(CH_3)_2$ | $CH_2$ | $CH_2$ | $CH(OC(O)CH_3)$ | C=C | |
| 2.27 | CH3 | H | H | $C(CH_3)(CH_2OH)$ | $CH_2$ | $CH_2$ | $CH(OC(O)CH_3)$ | C=C | |
| 2.28 | CH3 | H | H | $CH_2$ | $CH_2$ | $CH_2$ | $CH(CH_3)$ | C=C | |
| 2.29 | CH3 | H | H | $CH(CH_3)$ | $CH_2$ | $CH_2$ | $CH(CH_3)$ | C=C | |
| 2.30 | CH3 | H | H | $C(CH_3)_2$ | $CH_2$ | $CH_2$ | $CH(CH_3)$ | C=C | |
| 2.31 | CH3 | H | H | $C(CH_3)(CH_2OH)$ | $CH_2$ | $CH_2$ | $CH(CH_3)$ | C=C | |
| 2.32 | H | OH | H | $CH_2$ | $CH_2$ | $CH_2$ | $CH_2$ | C=C | |
| 2.33 | H | OH | H | $CH(CH_3)$ | $CH_2$ | $CH_2$ | $CH_2$ | C=C | |
| 2.34 | H | OH | H | $C(CH_3)_2$ | $CH_2$ | $CH_2$ | $CH_2$ | C=C | |
| 2.35 | H | OH | H | $C(CH_3)(CH_2OH)$ | $CH_2$ | $CH_2$ | $CH_2$ | C=C | |
| 2.36 | H | OH | H | $CH_2$ | $CH_2$ | $CH_2$ | $CH(OH)$ | C=C | |
| 2.37 | H | OH | H | $CH(CH_3)$ | $CH_2$ | $CH_2$ | $CH(OH)$ | C=C | |
| 2.38 | H | OH | H | $C(CH_3)_2$ | $CH_2$ | $CH_2$ | $CH(OH)$ | C=C | |
| 2.39 | H | OH | H | $C(CH_3)(CH_2OH)$ | $CH_2$ | $CH_2$ | $CH(OH)$ | C=C | |
| 2.40 | H | OH | H | $CH_2$ | $CH_2$ | $CH_2$ | $CH(OC(O)CH_3)$ | C=C | |
| 2.41 | H | OH | H | $CH(CH_3)$ | $CH_2$ | $CH_2$ | $CH(OC(O)CH_3)$ | C=C | |
| 2.42 | H | OH | H | $C(CH_3)_2$ | $CH_2$ | $CH_2$ | $CH(OC(O)CH_3)$ | C=C | |
| 2.43 | H | OH | H | $C(CH_3)(CH_2OH)$ | $CH_2$ | $CH_2$ | $CH(OC(O)CH_3)$ | C=C | |
| 2.44 | H | OH | H | $CH_2$ | $CH_2$ | $CH_2$ | $CH(CH_3)$ | C=C | |
| 2.45 | H | OH | H | $CH(CH_3)$ | $CH_2$ | $CH_2$ | $CH(CH_3)$ | C=C | |
| 2.46 | H | OH | H | $C(CH_3)_2$ | $CH_2$ | $CH_2$ | $CH(CH_3)$ | C=C | |
| 2.47 | H | OH | H | $C(CH_3)(CH_2OH)$ | $CH_2$ | $CH_2$ | $CH(CH_3)$ | C=C | |
| 2.48 | $CH_3$ | OH | H | $CH_2$ | $CH_2$ | $CH_2$ | $CH_2$ | C=C | |
| 2.49 | $CH_3$ | OH | H | $CH(CH_3)$ | $CH_2$ | $CH_2$ | $CH_2$ | C=C | |
| 2.50 | $CH_3$ | OH | H | $C(CH_3)_2$ | $CH_2$ | $CH_2$ | $CH_2$ | C=C | |
| 2.51 | $CH_3$ | OH | H | $C(CH_3)(CH_2OH)$ | $CH_2$ | $CH_2$ | $CH_2$ | C=C | |
| 2.52 | $CH_3$ | OH | H | $CH_2$ | $CH_2$ | $CH_2$ | $CH(OH)$ | C=C | |
| 2.53 | $CH_3$ | OH | H | $CH(CH_3)$ | $CH_2$ | $CH_2$ | $CH(OH)$ | C=C | |
| 2.54 | $CH_3$ | OH | H | $C(CH_3)_2$ | $CH_2$ | $CH_2$ | $CH(OH)$ | C=C | |
| 2.55 | $CH_3$ | OH | H | $C(CH_3)(CH_2OH)$ | $CH_2$ | $CH_2$ | $CH(OH)$ | C=C | |
| 2.56 | $CH_3$ | OH | H | $CH_2$ | $CH_2$ | $CH_2$ | $CH(OC(O)CH_3)$ | C=C | |
| 2.57 | $CH_3$ | OH | H | $CH(CH_3)$ | $CH_2$ | $CH_2$ | $CH(OC(O)CH_3)$ | C=C | |
| 2.58 | $CH_3$ | OH | H | $C(CH_3)_2$ | $CH_2$ | $CH_2$ | $CH(OC(O)CH_3)$ | C=C | |
| 2.59 | $CH_3$ | OH | H | $C(CH_3)(CH_2OH)$ | $CH_2$ | $CH_2$ | $CH(OC(O)CH_3)$ | C=C | |
| 2.60 | $CH_3$ | OH | H | $CH_2$ | $CH_2$ | $CH_2$ | $CH(CH_3)$ | C=C | |
| 2.61 | $CH_3$ | OH | H | $CH(CH_3)$ | $CH_2$ | $CH_2$ | $CH(CH_3)$ | C=C | |

TABLE 2-continued

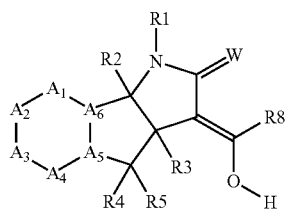

(II)

| Compound | R1 | R4 | R5 | $A_1$ | $A_2$ | $A_3$ | $A_4$ | $A_5$ | $A_6$ |
|---|---|---|---|---|---|---|---|---|---|
| 2.62 | $CH_3$ | OH | H | $C(CH_3)_2$ | $CH_2$ | $CH_2$ | $CH(CH_3)$ | C=C | |
| 2.63 | $CH_3$ | OH | H | $C(CH_3)(CH_2OH)$ | $CH_2$ | $CH_2$ | $CH(CH_3)$ | C=C | |
| 2.64 | H | $OC(O)CH_3$ | H | $CH_2$ | $CH_2$ | $CH_2$ | $CH_2$ | C=C | |
| 2.65 | H | $OC(O)CH_3$ | H | $CH(CH_3)$ | $CH_2$ | $CH_2$ | $CH_2$ | C=C | |
| 2.66 | H | $OC(O)CH_3$ | H | $C(CH_3)_2$ | $CH_2$ | $CH_2$ | $CH_2$ | C=C | |
| 2.67 | H | $OC(O)CH_3$ | H | $C(CH_3)(CH_2OH)$ | $CH_2$ | $CH_2$ | $CH_2$ | C=C | |
| 2.68 | H | $OC(O)CH_3$ | H | $CH_2$ | $CH_2$ | $CH_2$ | CH(OH) | C=C | |
| 2.69 | H | $OC(O)CH_3$ | H | $CH(CH_3)$ | $CH_2$ | $CH_2$ | CH(OH) | C=C | |
| 2.70 | H | $OC(O)CH_3$ | H | $C(CH_3)_2$ | $CH_2$ | $CH_2$ | CH(OH) | C=C | |
| 2.71 | H | $OC(O)CH_3$ | H | $C(CH_3)(CH_2OH)$ | $CH_2$ | $CH_2$ | CH(OH) | C=C | |
| 2.72 | H | $OC(O)CH_3$ | H | $CH_2$ | $CH_2$ | $CH_2$ | $CH(OC(O)CH_3)$ | C=C | |
| 2.73 | H | $OC(O)CH_3$ | H | $CH(CH_3)$ | $CH_2$ | $CH_2$ | $CH(OC(O)CH_3)$ | C=C | |
| 2.74 | H | $OC(O)CH_3$ | H | $C(CH_3)_2$ | $CH_2$ | $CH_2$ | $CH(OC(O)CH_3)$ | C=C | |
| 2.75 | H | $OC(O)CH_3$ | H | $C(CH_3)(CH_2OH)$ | $CH_2$ | $CH_2$ | $CH(OC(O)CH_3)$ | C=C | |
| 2.76 | H | $OC(O)CH_3$ | H | $CH_2$ | $CH_2$ | $CH_2$ | $CH(CH_3)$ | C=C | |
| 2.77 | H | $OC(O)CH_3$ | H | $CH(CH_3)$ | $CH_2$ | $CH_2$ | $CH(CH_3)$ | C=C | |
| 2.78 | H | $OC(O)CH_3$ | H | $C(CH_3)_2$ | $CH_2$ | $CH_2$ | $CH(CH_3)$ | C=C | |
| 2.79 | H | $OC(O)CH_3$ | H | $C(CH_3)(CH_2OH)$ | $CH_2$ | $CH_2$ | $CH(CH_3)$ | C=C | |
| 2.80 | $CH_3$ | $OC(O)CH_3$ | H | $CH_2$ | $CH_2$ | $CH_2$ | $CH_2$ | C=C | |
| 2.81 | $CH_3$ | $OC(O)CH_3$ | H | $CH(CH_3)$ | $CH_2$ | $CH_2$ | $CH_2$ | C=C | |
| 2.82 | $CH_3$ | $OC(O)CH_3$ | H | $C(CH_3)_2$ | $CH_2$ | $CH_2$ | $CH_2$ | C=C | |
| 2.83 | $CH_3$ | $OC(O)CH_3$ | H | $C(CH_3)(CH_2OH)$ | $CH_2$ | $CH_2$ | $CH_2$ | C=C | |
| 2.84 | $CH_3$ | $OC(O)CH_3$ | H | $CH_2$ | $CH_2$ | $CH_2$ | CH(OH) | C=C | |
| 2.85 | $CH_3$ | $OC(O)CH_3$ | H | $CH(CH_3)$ | $CH_2$ | $CH_2$ | CH(OH) | C=C | |
| 2.86 | $CH_3$ | $OC(O)CH_3$ | H | $C(CH_3)_2$ | $CH_2$ | $CH_2$ | CH(OH) | C=C | |
| 2.87 | $CH_3$ | $OC(O)CH_3$ | H | $C(CH_3)(CH_2OH)$ | $CH_2$ | $CH_2$ | CH(OH) | C=C | |
| 2.88 | $CH_3$ | $OC(O)CH_3$ | H | $CH_2$ | $CH_2$ | $CH_2$ | $CH(OC(O)CH_3)$ | C=C | |
| 2.89 | $CH_3$ | $OC(O)CH_3$ | H | $CH(CH_3)$ | $CH_2$ | $CH_2$ | $CH(OC(O)CH_3)$ | C=C | |
| 2.90 | $CH_3$ | $OC(O)CH_3$ | H | $C(CH_3)_2$ | $CH_2$ | $CH_2$ | $CH(OC(O)CH_3)$ | C=C | |
| 2.91 | $CH_3$ | $OC(O)CH_3$ | H | $C(CH_3)(CH_2OH)$ | $CH_2$ | $CH_2$ | $CH(OC(O)CH_3)$ | C=C | |
| 2.92 | $CH_3$ | $OC(O)CH_3$ | H | $CH_2$ | $CH_2$ | $CH_2$ | $CH(CH_3)$ | C=C | |
| 2.93 | $CH_3$ | $OC(O)CH_3$ | H | $CH(CH_3)$ | $CH_2$ | $CH_2$ | $CH(CH_3)$ | C=C | |
| 2.94 | $CH_3$ | $OC(O)CH_3$ | H | $C(CH_3)_2$ | $CH_2$ | $CH_2$ | $CH(CH_3)$ | C=C | |
| 2.95 | $CH_3$ | $OC(O)CH_3$ | H | $C(CH_3)(CH_2OH)$ | $CH_2$ | $CH_2$ | $CH(CH_3)$ | C=C | |

The compounds of Formula (I) according to the invention can be used as plant growth regulators or seed germination promoters by themselves, but they are generally formulated into plant growth regulation or seed germination promotion compositions using formulation adjuvants, such as carriers, solvents and surface-active agents (SFAs). Thus, the present invention further provides a plant growth regulator composition comprising a plant growth regulation compound of Formula (I) and an agriculturally acceptable formulation adjuvant. The present invention further provides a plant growth regulator composition consisting essentially of a plant growth regulation compound of Formula (I) and an agriculturally acceptable formulation adjuvant. The present invention further provides a plant growth regulator composition consisting of a plant growth regulation compound of Formula (I) and an agriculturally acceptable formulation adjuvant. The present invention further provides a seed germination promoter composition comprising a seed germination promoter compound of Formula (I) and an agriculturally acceptable formulation adjuvant. The present invention further provides a seed germination promoter composition consisting essentially of a seed germination promoter compound of Formula (I) and an agriculturally acceptable formulation adjuvant. The present invention further provides a seed germination promoter composition consisting of a seed germination promoter compound of Formula (I) and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of Formula (I) and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention still further provides a method for regulating the growth of plants in a locus, wherein the method comprises application to the locus of a plant growth regulating amount of a composition according to the present invention.

The present invention also provides a method for promoting the germination of seeds, comprising applying to the seeds, or to a locus containing seeds, a seed germination promoting amount of a composition according to the present invention.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound of Formula (I) or composition of the present invention may be applied to a plant, part of the plant, plant organ, plant propagation material or a surrounding area thereof.

In one embodiment, the invention relates to a method of treating a plant propagation material comprising applying to the plant propagation material a composition of the present invention in an amount effective to promote germination and/or regulate plant growth. The invention also relates to a plant propagation material treated with a compound of Formula (I) or a composition of the present invention. Preferably, the plant propagation material is a seed. Preferably, the plant propagation material is a seed. In an embodiment of the invention, the plant of the seed is selected from the genus *brassica*. The seed is in such an embodiment selected from the genus *brassica*. Common types of *brassica* include cabbage, cauliflower, broccoli, Brussel sprouts.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of formula (I) may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence.

The rates of application of compounds of Formula (I) may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of Formula (I) according to the invention are generally applied at a rate of from 1 to 2000 g/ha, especially from 5 to 1000 g/ha. For seed treatment the rate of application is generally between 0.0005 and 150 g per 100 kg of seed.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

The invention may also be used to regulate the growth, or promote the germination of seeds of non-crop plants, for example to facilitate weed control by synchronizing germination.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rending crop plants tolerant to HPPD-inhibitors are known, for example from WO0246387; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Compounds and compositions of the present invention may be applied in combination with other active ingredients or products for use in agriculture, including insecticides, fungicides, herbicides, plant growth regulators, crop enhancing compounds, nutrients and biologicals. Examples of suitable mixing partners may be found in the Pesticide Manual, 15$^{th}$ edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops.

In a further aspect of the present invention, the compounds or composition of the present invention may be applied in combination with one or more other compounds having a crop enhancement effect. Such compounds include micronutrients, saccharides, amino acids, flavonoids, quinines, and plant activators/growth stimulators. For example, such compounds include natural or synthetic hormones, auxins, brassinosteroids, gibberellins, abscisic acid, cytokinins, jasmonates, strigolactones, salicylic acid, ethylene, 1-methylcyclopropene, trinexapac-ethyl or derivatives thereof. Such compounds also include pesticides that have a crop enhancement effect, for example strobilurins (including azoxystrobin, pyraclostrobin), and neonicotinoids (including thiamethoxam, and imidacloprid).

It has now been found that these strigolactam derivatives according to the invention also show crop enhancement effects.

Accordingly, the present invention provides a method of enhancing and/or increasing the yield of crop plants by applying to the plants, plant parts, plant propagation material, or a plant growing locus, a compound of formula (I).

The term "increasing the yield" of a plant means that the yield of a product of the plant is increased by a measurable amount over the yield of the same product of the plant produced under the same conditions, but without the application of the combinations according to the present invention. It is preferred that the yield is increased by at least about 0.5%, preferably 1%, more preferably 2%, yet more preferably 4% or more. Even more preferred is an increase in yield of at least about 5%, 10%, 15% or 20% or more.

According to the present invention, 'crop enhancement' means an improvement in plant vigour, an improvement in plant quality, improved tolerance to stress factors, and/or improved input use efficiency.

According to the present invention, an 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

According to the present invention, an 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

According to the present invention, an 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

According to the present invention, an 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other crop enhancements of the present invention include a decrease in plant height, or reduction in tillering, which are beneficial features in crops or conditions where it is desirable to have less biomass and fewer tillers.

Crop enhancement also includes safening of crop plants against phytotoxic effects of pesticides or other compounds that are applied to the crop.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

According to the present invention, there is provided the use of a compound of formula (I) or a composition comprising a compound of formula (I) for improving plant yield, plant vigour, plant quality, plant tolerance to stress factors and/or plant input use efficiency.

Crop enhancement may be achieved in a range of crops. Suitable target crops are, in particular, cereals, such as wheat, barley, rye, oats, rice, maize or sorghum. However, preferably the crop plants are selected from the group consisting of corn, wheat, rice, soybean.

The compounds of the invention may be made by the following methods.

SCHEME 1

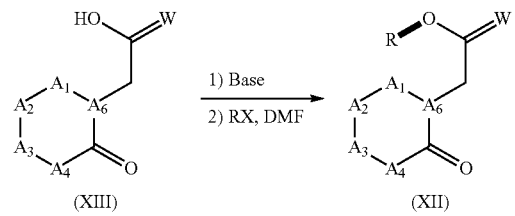

Compounds of formula (XII) within R are $C_1$-$C_6$ alkyl and W is oxygen may be prepared from compounds of Formula (XIII) by esterification by treatment with an alcohol in presence of an acid, such sulphuric acid in methanol or ethanol. Alternatively, compounds of formula (XII) within R are benzyl and W is oxygen may be prepared from compounds of formula (XIII) by reaction with benzylbromide in presence of a base such as cesium carbonate. Compounds of formula (XIII) are either known compounds or may be made by methods known to a person skilled in the art.

SCHEME 2 A

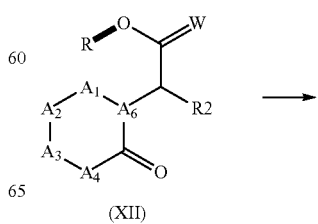

21

-continued

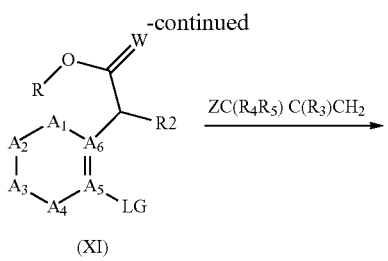

(XI)

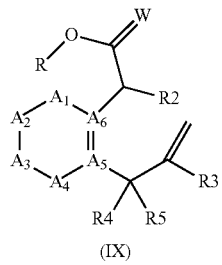

(IX)

Compounds of formula (XI) wherein R is a alkyl or benzyl may be made by treatment of compounds of formula (XII) by reaction with a reagent such as triflic anhydride or N,N-bis (trifluoromethylsulfonyl)-5-chloro-2-pyridylamine in presence of a base such as lithium diisopropylamide.

Alternatively, compounds of formula (XI) wherein $A_1$ is C—($C_1$-$C_6$ alkyl) might be prepared from compound (XII) wherein $A_1$-$A_6$ is a double bound by reaction with an organometallic such as an organo cuprate, followed by reaction of the resulting enolate with a reagent such as as triflic anhydride or N,N-bis(trifluoromethyl sulfonyl)-5-chloro-2-pyridylamine. The desired organocuprate can be prepared from the corresponding organo lithium or organo magnesium by methods known to a person skilled in the art.

Compounds of Formula (IX), wherein R is alkyl may be made by treatment of compounds of Formula (XI), wherein LG is a leaving group such as OTf with a allyl derivative of

22 formula $ZC(R_4R_5)C(R_3)CH_2$, Wherein Z is a boron or a tin derivatives in the presence of a suitable catalyst/ligand system, often a palladium (0) complex.

Scheme 2B:

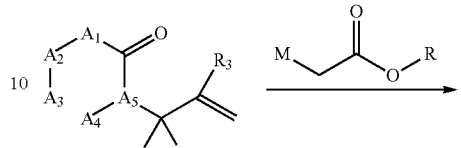

(X)

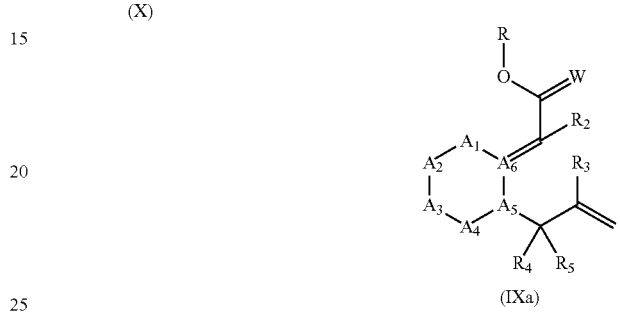

(IXa)

Alternatively, compounds or formula (IXa) wherein R is alkyl and W=O can be prepared from compound of formula (IXa) by olefination of the ketone with a phosphonate of formula $MCH_2CO_2R$ wherein $M=PO(OR')_2$ or a silane reagent of formula $MCH_2CO_2R$ wherein $M=SiR'_3$ in the presence of a base such as LDA. These reactions are known by a person skilled in the art as WHO olefination or Peterson olefination

SCHEME 3

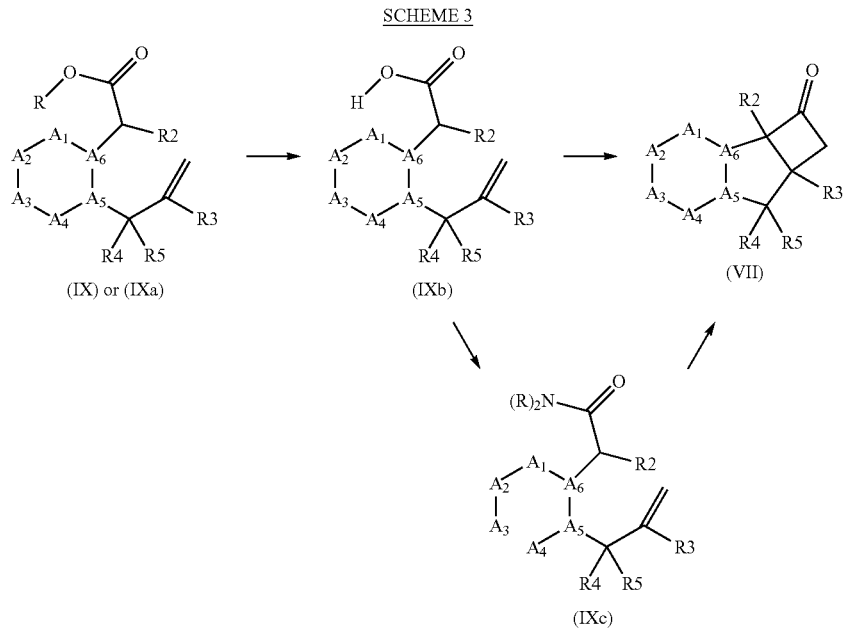

Compounds of Formula (VII) may be made by treatment of compounds of Formula (IXb) with a reagent used for the synthesis of acyl chloride such as (1-chloro-2-methyl-propenyl)-dimethyl-amine, followed by reaction with a base such as triethylamine. The formation of acyl chloride is very well known, to a person skilled in the art and could be done with many other reagents such as thionyl chloride, oxalyl chloride or phosphorus trichloride. The second reaction is known, to a person skilled in the art by processing via an intramolecular ketene cycloaddition.

Alternatively, compounds of Formula (VII) may be prepared by treatment of compounds of formula (IXc) with a dehydrating agent such as triflic anhydride in presence of a base such as collidine to give a ketene iminium intermediate with subsequent intramolecular cycloaddition and followed by hydrolysis of the resulting imine with water.

Compounds of formula (IXb) may be made by treatment of compounds of formula (IX) or (IXa), wherein R is $C_1$ to $C_6$ alkyl or benzyl by hydrolysis of the ester group with a base such as sodium hydroxide or lithium hydroxide.

Compounds of formula (IXc) can be prepared from compounds of formula (IXb) by reaction with an amine of formula $HN(R)_2$ wherein R is not cyclic such as methyl or $(R)_2$ is cyclic such as pyrrolidine. The reactions may be carried out in the presence of a coupling reagent, such as DCC(N,N'-dicyclohexyl¬carbo¬diimide), EDC (1-ethyl-3-[3-dimethyl¬amino-propyl]carbodiimide hydrochloride) or BOP-Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole or 1-hydroxy-7-azabenzotriazole. Alternatively, the reaction may be conducted in a biphasic system comprising an organic solvent, preferably ethyl acetate, and an aqueous solvent, preferably a solution of sodium bicarbonate. When R is $C_1$-$C_6$alkoxy the ester (IX) may be converted directly to the amide by heating the ester and amine together in a thermal process. The amines of formula $(R)_2NH$ are either known compounds or may be made by methods known to a person skilled in the art.

Compounds of formula (VIa), wherein R1 is H, may be prepared from a compound of formula (VII) by reaction with a compound of formula (VIII) wherein X is a leaving group such as OH, OTs, OMes, OMs or Cl in presence of a Lewis acid or a Brönsted acid. This reaction is very well known, to a person skilled in the art under the name of Beckmann rearrangement.

Compounds of formula (VI), wherein R1 is alkyl derivatives or benzyl derivatives may be prepared from a compound of formula (VIa) wherein R1 is H via alkylation by reaction of the amine with an alkylating agent (III), R1X where X is halogen or tosyl group, such as an alkyl halide, benzyl halide optionally in the presence of a base such as sodium hydride.

Compounds of formula (VI), wherein a carbonyl derivative, may be prepared from a compound of formula (VIa) wherein R1 is H via acylation with a compound of formula (IV), wherein R is OH, in the presence of a coupling reagent, such as DCC(N,N'-dicyclohexylcarbodiimide), EDC (1-ethyl-3-[3-dimethylamino-propyl]carbodiimide hydrochloride) or BOP-Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. Optionally, when R is Cl or $OC(O)C_1$-$C_6$alkoxy, the acylation reaction may be carried out under basic conditions (for example in the presence of pyridine, triethylamine, 4-(dimethylamino)pyridine or diisopropylethylamine), optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. Optionally, when R is $C_1$-$C_6$ alkoxy, the amide may be prepared by heating the ester analogue of compound Formula (IV) and amide (VIa) together. R' may be alkyl or alkoxy group.

Compounds of Formula (VI) wherein R1 is aryl or heteroaryl can be prepared from compounds of Formula (VIa) wherein R1 is H and the correspond aryl halide or heteroaryl halide in the presence of a base such as sodium hydride or potassium carbonate, and eventually a catalyst, often a Pd(0) complex or a copper(1) complex a ligand such as dimethylethane-1,2-diamine.

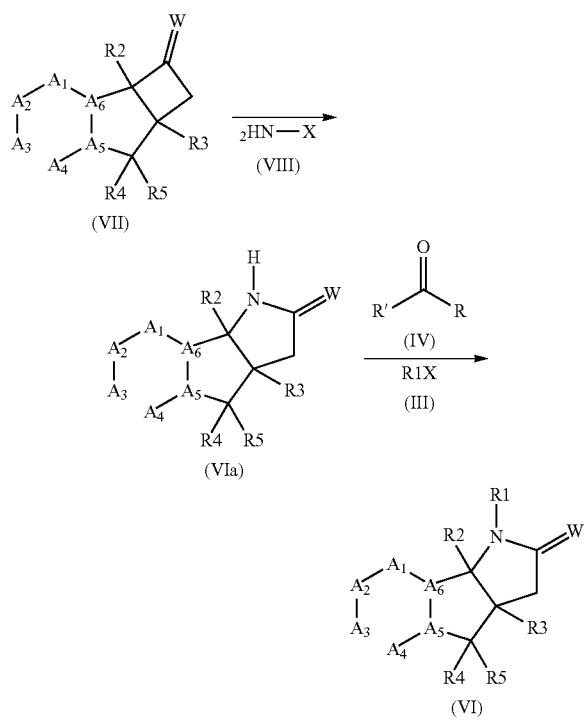

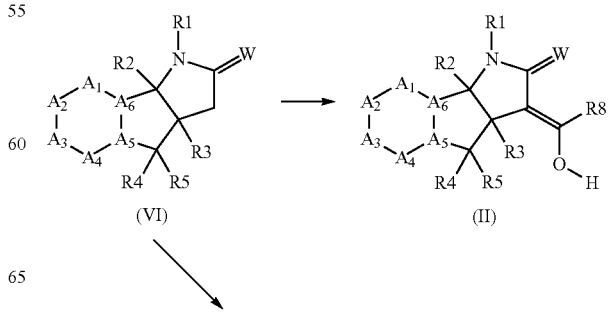

-continued

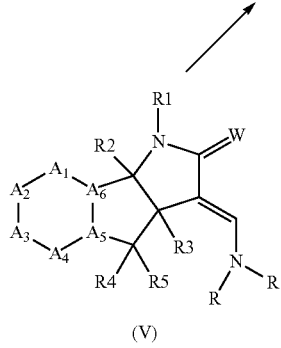

(V)

Compounds of formula (II) may be prepared from a compound of formula (VI) via reaction with a formic ester derivative such as the ethyl formate in presence of a base such as lithium diisopropylamide or lithium bis(trimethylsilyl) amide. Alternatively, compounds of formula (II) may be prepared from a compound of formula (V) via hydrolysis with an acid such as hydrogen chloride. Compounds of formula (V) may be prepared from a compounds of formula (VI) via reaction with a Bredereck's reagent (t-butoxybis(dimethylamino)methane) wherein R is methyl or analogue.

SCHEME 6

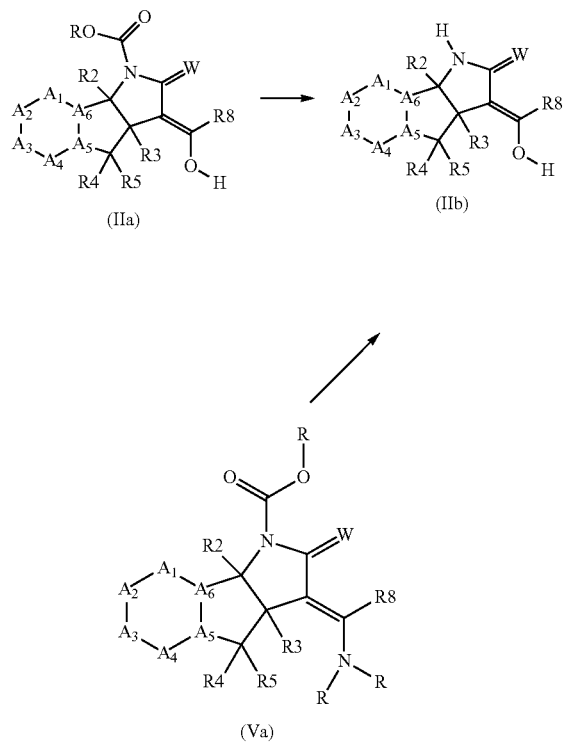

Compounds of Formula (IIb) can be prepared from a compound of Formula (IIa) wherein R is an alkyl group such as tert butyl via treatment with an acid such as trifluoroacetic acid or Hydrogen chloride. Alternatively, Compounds of Formula (IIb) can be prepared from a compound of Formula (Va) wherein R is an alkyl group such as tert butyl via treatment with an acid such as hydrogen chloride.

SCHEME 7

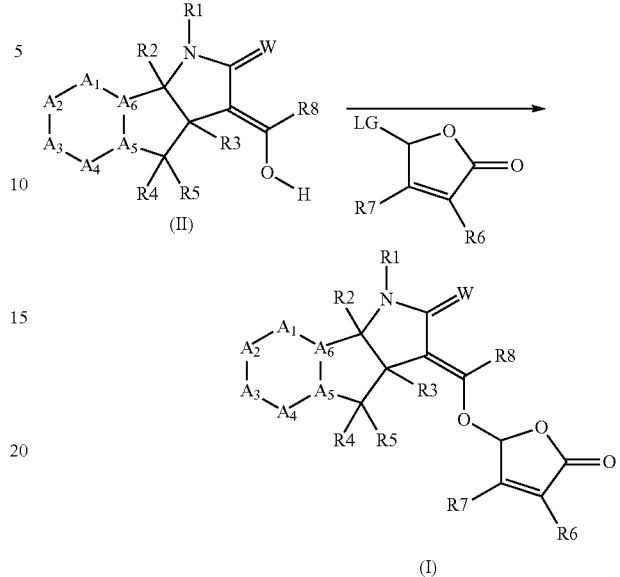

Compounds of Formula (I) may be prepared from a compounds of Formula (II) via nucleophilic substitution of a 5H-furanone derivative having a leaving group (LG) and LG is a leaving group, such as bromine or chlorine in position 5 in presence of a base such as for example potassium tert-butylate and with or without an additive such as 18-crown-6.

SCHEME 8

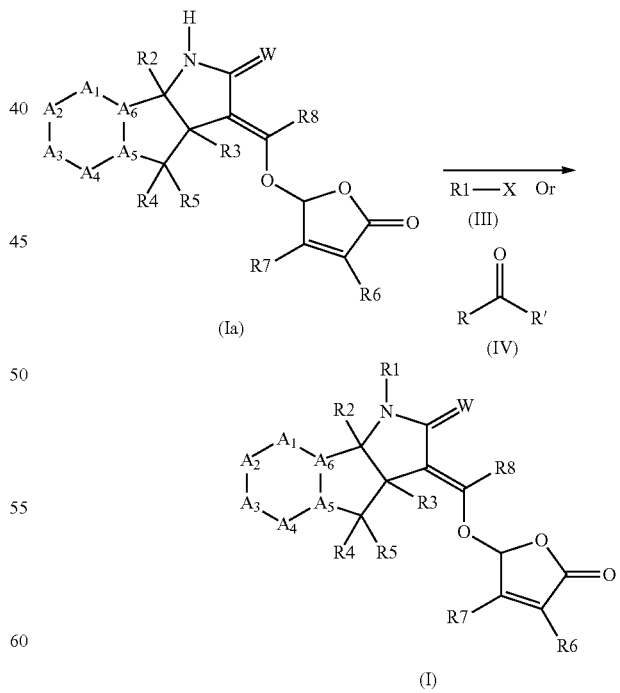

Alternatively, compounds of Formula (I), wherein R1 is an alkyl derivative or benzyl derivative, may be prepared from a compound of Formula (Ia) wherein R1 is H via alkylation by reaction of the amine with an alkylating agent (III) such as an alkyl halide, benzyl halide optionally in the presence of a base such as sodium hydride or silver oxide.

Alternatively, compounds of Formula (I) may be prepared from a compound of Formula (Ia) wherein R1 is H via acylation with a compound of Formula (IV), wherein R is OH, in the presence of a coupling reagent, such as DCC(N,N'-dicyclohexylcarbodiimide), EDC (1-ethyl-3-[3-dimethylaminopropyl]carbodiimide hydrochloride) or BOP-Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. Optionally, when R is Cl or $OC(O)C_1$-$C_6$alkoxy, the acylation reaction may be carried out under basic conditions (for example in the presence of pyridine, triethylamine, 4-(dimethylamino)pyridine or diisopropylethylamine), optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. Optionally, when R is $C_1$-$C_6$alkoxy, the amide may be prepared by heating the ester (IV) and amide (Ia) together.

Compounds of Formula (I), wherein W is sulfur, may be prepared from a compound of Formula (I), wherein W is oxygen, by treatment with a thio-transfer reagent, such as Lawesson's reagent or phosphorus pentasulfide.

Compound of formula (Ia) might be prepared from compound of formula (Ib) by treatment with an acid such as HCl or a Lewis acid such as magnesium chloride.

EXAMPLES

The following HPLC-MS methods were used for the analysis of the compounds:

Method A:

Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Agilent 1100 LC (Solvent degasser, binary pump, heated column compartment and diode-array detector. Column: Phenomenex Gemini C18, 3 μm, 30×3 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 0% B; 2-2.8 min 100% B; 2.9-3 min 0% B. Flow (ml/min) 1.7

Method B:

Spectra were recorded on a SQD Mass Spectrometer from Waters (Single quadrupole mass spectrometer) mass spectrometer equipped with an electrospray source (Polarity: positive and negative ions, Capillary: 3.00 kV, Cone: 30.00 V, Extractor: 2.00 V, Source Temperature: 150° C., Desolvation Temperature: 250° C., Cone Gas Flow: 0 L/Hr, Desolvation Gas Flow: 650 L/Hr, Mass range: 100 to 900 Da) and an Acquity UPLC from Waters (Binary pump, heated column compartment and diode-array detector, Solvent degasser, binary pump, heated column compartment and diode-array detector, Column: Phenomenex Gemini C18, 3 μm, 30×2 mm, Temp: 60° C., flow rate 0.85 mL/min; DAD Wavelength range (nm): 210 to 500) Solvent Gradient: A=$H_2O$+5% MeOH+0.05% HCOOH, B=Acetonitril+0.05% HCOOH) gradient: 0 min 0% B; 0-1.2 min 100% B; 1.2-1.50 min 100% B.

Method C:

Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 150° C., Desolvation Temperature: 350° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 10% B; 1.2-1.50 min 100% B. Flow (ml/min) 0.85

The following abbreviations are used throughout this section: s=singlet; bs=broad singlet; d=doublet; dd=double doublet; dt=double triplet; t=triplet; tt=triple triplet, q=quartet, m=multiplet; Me=methyl; Et=ethyl; Pr=propyl; Bu=butyl; M.p.=melting point; RT=retention time, $MH^+$=molecular cation (i.e. measured molecular weight).

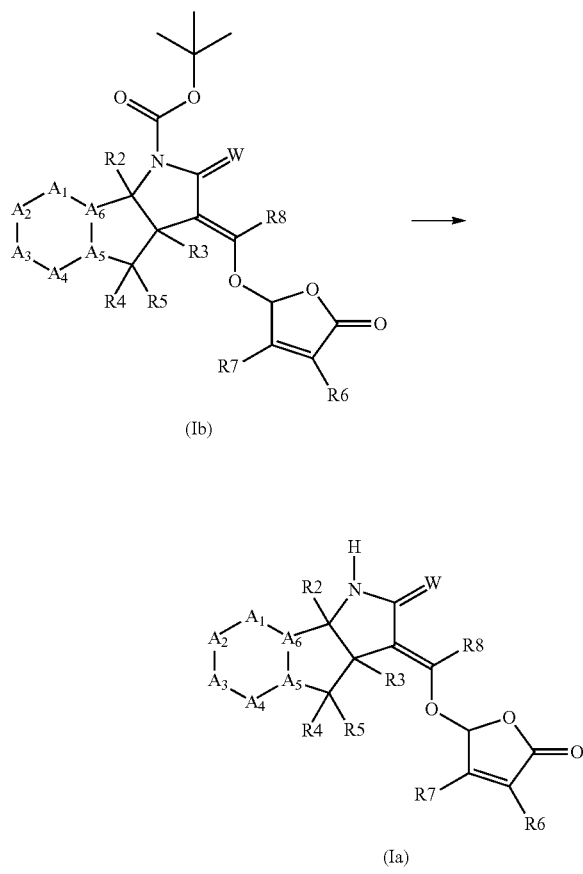

SCHEME 9

(Ib)

(Ia)

Example 1

(3E,3aR,8bS)-8,8-dimethyl-3-[(4-methyl-5-oxo-2H-furan-2-yl)oxymethylene]-3a,4,5,6,7,8b-hexahydro-1H-indeno[1,2-b]pyrrol-2-one (P1)

Step 1

Benzyl 2-(2-methyl-6-oxo-cyclohexen-1-yl)acetate

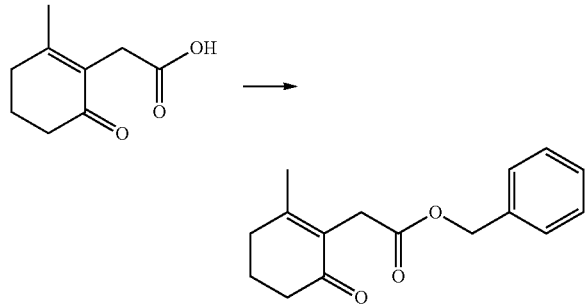

A solution of the acid (Org. Proc. Research & Dev 1997, p. 222) (2.0 g, 11.9 mmol) in MeOH (20 mL) was stirred with caesium carbonate (1.93 g, 5.94 mmol) for 1 h and the solvents were removed in vacuo. The residue was taken up in DMF (20 mL) and benzyl bromide (1.84 mL, 15.5 mmol) was added. The solution was stirred overnight at room temperature. The solution was diluted with diethylether (100 mL) and the precipitate was removed by filtration. The filtrate was washed with brine (3*50 mL), dried and concentrated. The residue was purified by flash chromatography eluting with cyclohexane and ethyl actetate (9/1 to 4/1) to give the desired compound as a colourless oil (2.8 g, 90%); $^1$H NMR (400 MHz, CHLOROFORM-d) 7.31-7.41 (5H, m), 5.12 (2H, s), 3.43 (2H, s), 2.42 (4H, s), 1.99 (2H, quin, J=6.2 Hz), 1.93 (3H, s).

Step 2

Benzyl 2-[6,6-dimethyl-2-(trifluoromethylsulfonyloxy)cyclohexen-1-yl]acetate

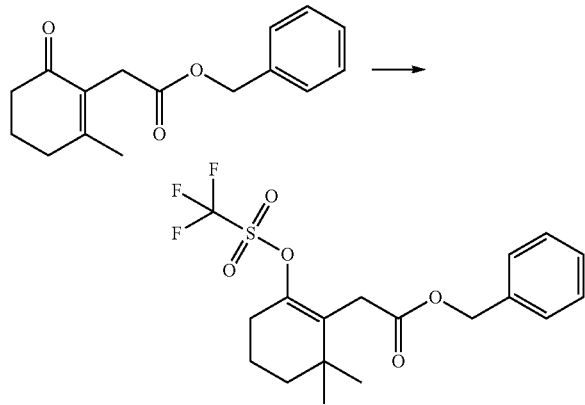

To a suspension of copper iodide (1.66 g, 8.71 mmol) in diethylether (20 mL) cooled at −20° C. was added methyl lithium (1.6 M in diethylether, 10.8 mL, 17.4 mmol) slowly. The solution was stirred for 30 min at −15° C., until the copper iodide was completely dissolved and the benzyl 2-(2-methyl-6-oxo-cyclohexen-1-yl)acetate (1.50 g, 5.80 mmol) in diethylether (5 mL) was then added at −20° C. The solution was stirred for 10 min at −20° C. Then, bis(trifluoromethylsulfonyl)-5-chloro-2-pyridylamine reagent (2.73 g, 7.00 mmol) was added in THF (10 mL) and the solution was stirred for 15 min at 0° C. Saturated ammonium chloride was added followed by hexane/ethyl acetate (9/1, 100 mL). The blue/white precipitate was filtered and the filtrate was extracted with a mixture of hexane and ethyl acetate (9/1). The combined organic layers were washed with brine, dried and concentrated. The residue was purified by flash chromatography eluting with cyclohexane and ethyl acetate (25/1) to give the title compound as a colourless oil (1.90 g, 80%). $^1$H NMR (400 MHz, CDCl$_3$) δ 7.30-7.44 (5H, m), 5.15 (2H, s), 3.22 (2H, s), 2.43 (2H, t, J=6.4 Hz), 1.79 (2H, m), 1.52 (2H, m), 1.03 (6H, s) ppm.

Step 3

Benzyl 2-(2-allyl-6,6-dimethyl-cyclohexen-1-yl)acetate

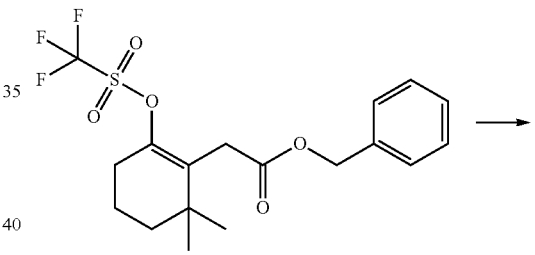

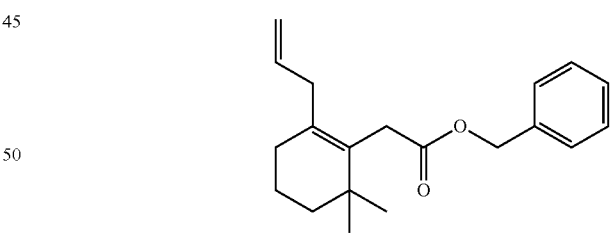

A solution of benzyl 2-[6,6-dimethyl-2-(trifluoromethylsulfonyloxy)cyclohexen-1-yl]acetate (2.30 g, 5.66 mmol) in dioxane (10 mL) was purged with argon. Then, allyl stannane (2.10 mL, 6.79 mmol), palladium triphenylphosphine tetrakis (327 mg, 0.28 mmol) and lithium chloride (360 mg, 8.49 mmol) were added. The solution was heated to reflux for 7 h and was then concentrated to give a crude yellow oil, which was purified by flash chromatography eluting with cyclohexane and ethyl acetate (25/1) to give the title compound as a colourless oil (1.55 g, 92%). $^1$H NMR (400 MHz, CDCl$_3$) δ 7.33-7.40 (5H, m), 5.72 (1H, ddt, J=16.8, 10.5, 6.2 Hz), 5.11 (2H, s), 4.97 (1H, dt, J=16.8, 1.5 Hz), 4.96 (1H, dt, J=10.5, 1.5

Hz), 3.11 (2H, s), 2.71 (2H, d, J=6.2 Hz), 2.00 (2H, t, J=6.2 Hz), 1.58-1.65 (2H, m), 1.46-1.50 (2H, m), 0.97 (6H, s) ppm.

Step 4

2-(2-Allyl-6,6-dimethyl-cyclohexen-1-yl)acetic acid

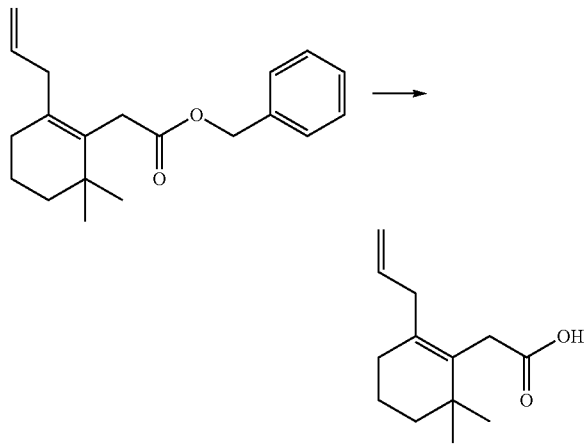

To a solution of benzyl 2-(2-allyl-6,6-dimethyl-cyclohexen-1-yl)acetate (1.5 g, 5.02 mmol) in dioxane (12 mL) and water (4 mL) was added NaOH (2M, 5.5 mL). The solution was heated to 100° C. for 30 h. The solution was concentrated in vacuo and water was added. The aqueous layer was extracted 2 times with ether and the organic layer was removed. Then, pH of the aqueous layer was adjusted to 1. The solution was extracted with ethyl acetate and washed with brine, dried and concentrated to give the desired product as a colourless oil (1.05 g, quant). $^1$H NMR (400 MHz, CDCl$_3$) δ 5.77 (1H, dd, J=16.9, 10.3 Hz), 4.88-5.09 (2H, m), 3.13 (2H, s), 2.74 (2H, d, J=6.2 Hz), 1.96-2.08 (2H, m), 1.59-1.69, (2H, m), 1.43-1.57 (2H, m), 0.98-1.06 (6H, s) ppm.

Step 5

2-(2-Allyl-6,6-dimethyl-cyclohexen-1-yl)-1-pyrrolidin-1-yl-ethanone

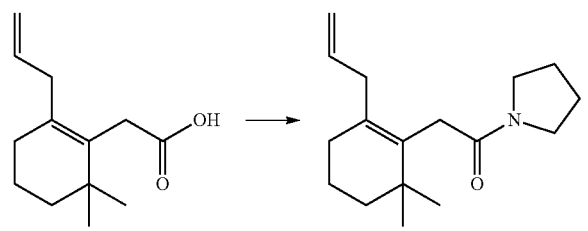 [SMILES: C=CCC1=C(CC(=O)O)C(C)(C)CCC1 ; C=CCC1=C(CC(=O)N2CCCC2)C(C)(C)CCC1]

To a solution of 2-(2-allyl-6,6-dimethyl-cyclohexen-1-yl) acetic acid (80 mg, 0.38 mmol), 1-ethyl-3-(3-dimethylaminopropyl)carbodiimide (103 mg, 0.54 mmol) and 1-hydroxy-7-azabenzotriazole (73 mg, 0.54 mmol) in DMF (2 mL) was added the pyrrolidine (55 mg, 0.77 mmol) followed by Et$_3$N (117 mg, 1.15 mmol). The solution was stirred under Ar for 18 h. Water was added (20 mL) and the solution was extracted with ether (3*20 mL). The combined organic layers were washed with water (3*30 mL) and brine, dried and concentrated. The residue was purified by flash chromatography eluting with cyclohexane and ethyl acetate (4-1 to 3/1) to give the title compound as colourless oil (82 mg, 82%). $^1$H NMR (400 MHz, CDCl$_3$) δ 5.75 (1H, ddt, J=16.7, 10.5, 6.1, 6.1 Hz), 4.93 (2H, m, J=19.1, 1.8 Hz), 4.93 (0H, dd, J=8.1, 1.8 Hz), 3.44 (4H, td, J=6.8, 4.0 Hz), 2.93 (2H, s), 2.64 (2H, d, J=5.9 Hz), 1.89-2.02 (4H, m), 1.82 (2H, quin, J=6.6 Hz), 1.58 (2H, d, J=11.7 Hz), 1.43-1.50 (2H, m) 0.90-0.99 (6H, s) ppm.

Step 6

3,3-Dimethyl-2a,4,5,6,7,7a-hexahydro-1H-cyclobuta[a]inden-2-one

Method 1

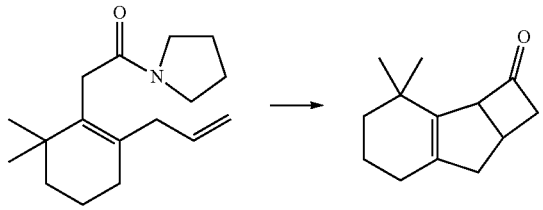 [SMILES: C=CCC1=C(CC(=O)N2CCCC2)C(C)(C)CCC1 ; CC1(C)CCCC2=C1C1C(=O)CC1C2]

To a solution of 2-(2-allyl-6,6-dimethyl-cyclohexen-1-yl)-1-pyrrolidin-1-yl-ethanone (60 mg, 0.23 mmol) in dichloromethane (3 mL) was added collidine (31 mg, 0.25 mmol) followed by a solution of triflic anhydride (71 mg, 0.25 mmol) in dichloromethane (1 mL). The solution was stirred for 4 h at room temperature. Collidine (31 mg, 0.25 mmol) and triflic anhydride (71 mg, 0.25 mmol) were added again and the solution was stirred for 1 h. Solvents were removed in vacuo and the residue was taken up in carbon tetrachloride (2 mL) and water (2 mL). The biphasic mixture was heated to reflux for 2 h. Dichloromethane (20 mL) was added and the aqueous layer was extracted with dichloromethane (20 mL). The combined organic layers were dried (Na2SO4) and concentrated. The residue was purified by Flash chromatography eluting with 5% ethyl acetate in cyclohexane to give 32 mg of a colourless oil (79%). $^1$H NMR (400 MHz, CDCl$_3$) δ 4.11-4.22 (1H, m), 3.08 (1H, ddd, J=17.2, 7.7, 4.8 Hz), 2.56-2.75 (3H, m), 2.21 (2H, dd, J=16.1, 3.7 Hz), 1.85-1.97 (2H, m), 1.59 (2H, quin, J=6.2 Hz), 1.26-1.43 (2H, m), 0.95 (6H, s) ppm; ES+: 191 (M+H+)

Method 2

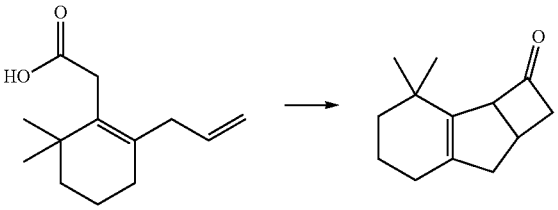

To a solution of 2-(2-allyl-6,6-dimethyl-cyclohexen-1-yl) acetic acid (424 mg, 2.04 mmol) in dichloromethane (50 mL) was added Ghosez' reagent (326 mg, 2.44 mmol). The solution was stirred for 1 h and then heated to reflux. A solution of triethylamine (0.567 mL, 4.08 mmol) in dichloromethane (1 mL) was then slowly added over 5 min and the solution was heated at reflux for 2 h. The solution was then cooled down to room temperature and more dichloromethane was added (20 mL). The solution was washed with HCl (1M), dried and concentrated. The residue was purified by flash chromatography eluting with 5% ethyl acetate in cyclohexane to give 310 mg of a colourless oil (79%) (data identical to method A).

Step 7

8,8-Dimethyl-1,3,3a,4,5,6,7,8b-octahydroindeno[1,2-b]pyrrol-2-one

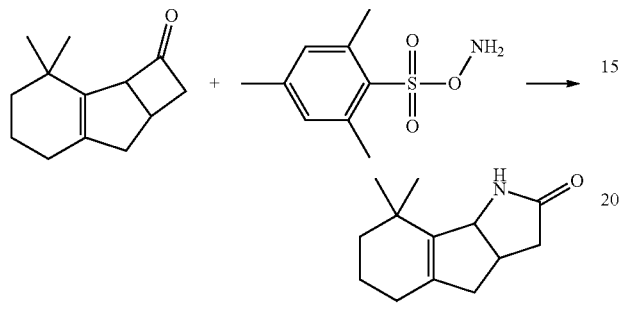

To a solution of 3,3-dimethyl-2a,4,5,6,7,7a-hexahydro-1H-cyclobuta[a]inden-2-one (150 mg, 0.79 mmol) in dichloromethane (3 mL) was added amino 2,4,6-trimethylbenzenesulfonate (60% in water, 0.280 mg, 0.86 mmol) (Organic Process Research and Development 2009, p. 263). The solution was stirred at room temperature for 1 h and the solution was diluted with dichloromethane (10 mL) and washed with saturated NaHCO$_3$. The organic layer was dried and concentrated to give the desired lactam as a white solid (200 mg, quant.). The residue was used without further purification in the next step. LCMS (Method A) RT=1.61 min, 206 (M+H$^+$); $^1$H NMR (400 MHz, CDCl$_3$) δ 6.26 (1H, br. s.), 4.53 (1H, d, J=7.0 Hz), 2.80-3.02 (1H, m), 2.50-2.69 (2H, m), 2.05-2.22 (2H, m), 1.92 (2H, q, J=6.2 Hz), 1.57-1.78 (2H, m) 1.30-1.50 (2H, m), 1.05 (3H, s), 1.04 (3H, s) ppm.

Step 8

Tert-butyl 8,8-dimethyl-2-oxo-3a,4,5,6,7,8b-hexahydro-3H-indeno[1,2-b]pyrrole-1-carboxylate

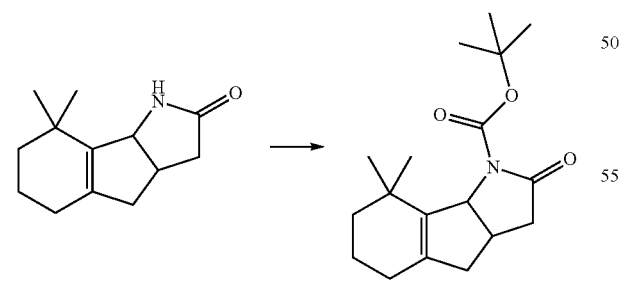

To a solution of crude 8,8-dimethyl-1,3,3a,4,5,6,7,8b-octahydroindeno[1,2-b]pyrrol-2-one (200 mg, 0.974 mmol) in dichloromethane (10 mL) was added di-tert-butyl dicarbonate (414 mg, 1.94 mmol), Et$_3$N (0.272 mL, 1.94 mmol) and N,N-dimethylaminopyridine (12 mg, 0.097 mmol). The solution was stirred for 24 h. The solution was washed with 1N HCl, dried and concentrated. The residue was purified by flash chromatography eluting with ethyl acetate and cyclohexane (1/9 to 3/7) to give 133 mg of yellow oil (55% over 2 steps). LCMS (Method B) RT=1.17 min, 634 (2M+Na+); $^1$H NMR (400 MHz, CDCl$_3$) δ 5.31 (1H, d, J=7.3 Hz), 2.84 (1H, ddd, J=16.5, 9.2, 7.3 Hz), 2.65 (1H, dd, J=17.6, 9.2 Hz), 2.41 (1H, dd, J=16.1, 7.0 Hz), 2.25 (1H, dd, J=17.6, 10.3 Hz), 2.01 (3H, s), 1.53-1.66 (11H, m), 1.39-1.52 (2H, m), 1.16 (3H, s), 0.99 (3H, s) ppm.

Step 9

Tert-butyl (3E)-3-(dimethylaminomethylene)-8,8-dimethyl-2-oxo-3a,4,5,6,7,8b-hexahydroindeno[1,2-b]pyrrole-1-carboxylate

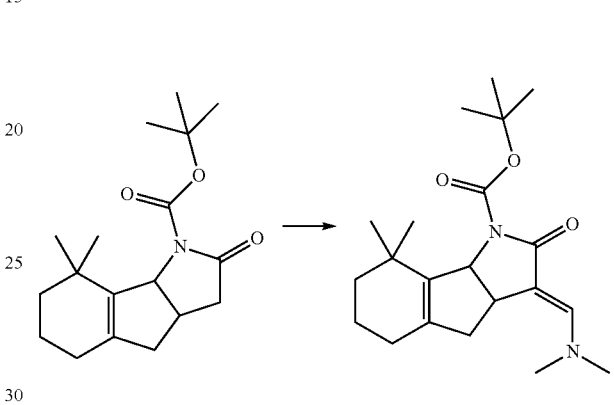

To a solution of tert-butyl 8,8-dimethyl-2-oxo-3a,4,5,6,7,8b-hexahydro-3H-indeno[1,2-b]pyrrole-1-carboxylate (110 mg, 0.36 mmol) in toluene (2 mL) was added Bredereck reagent ((t-butoxybis(dimethylamino)methane) (0.30 mL, 1.44 mmol). The solution was heated to 110° C. for 5 h. The solution was cooled down to room temperature, and water was added. The solution was extracted with ethyl acetate, washed with brine, dried and concentrated. The residue was purified by flash chromatography eluting with cyclohexane and ethyl acetate (7/3 to 1/1) to give a white solid (83 mg, 64%). Mp 170-172° C.; LCMS (Method B) RT=1.14 min, 361 (M+H+); $^1$H NMR (400 MHz, CDCl$_3$) δ 7.10 (1H, d, J=1.8 Hz), 5.27 (1H, d, J=8.1 Hz), 3.65 (1H, tt, J=8.1, 1.8 Hz), 2.99 (6H, s), 2.24 (1H, d, J=15.4 Hz), 1.75-1.97 (2H, m), 1.49-1.60 (11H, m), 1.38-1.46 (1H, m), 1.32 (1H, m), 1.19 (3H, s), 0.97 (3H, s) ppm.

Step 10

(3E)-3-(Hydroxymethylene)-8,8-dimethyl-3a,4,5,6,7,8b-hexahydro-1,1-indeno[1,2-b]pyrrol-2-one

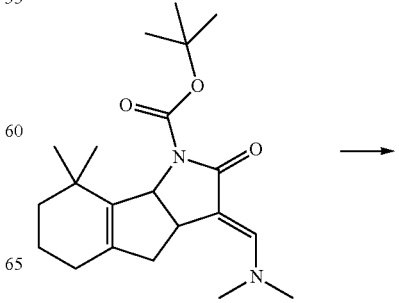

-continued

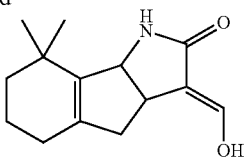

To a solution of tert-butyl (3E)-3-(dimethylaminomethylene)-8,8-dimethyl-2-oxo-3a,4,5,6,7,8b-hexahydroindeno[1,2-b]pyrrole-1-carboxylate (83 mg, 0.23 mmol) in THF (2 mL) was added 1N HCl (0.35 mmol). The solution was stirred for 3 h at room temperature and water was added. The solution was extracted with ethyl acetate (2*30 mL), washed with brine, dried and concentrated to give the yellow oil (78 mg, quant.). This product was taken up in dichloromethane (2 mL) at 0° C. and trifluoroacetic acid (0.2 mL) was added. The solution was stirred at 0° C. for 30 min and saturated NaHCO$_3$ was added. The solution was extracted with dichloromethane, dried and concentrated to give the title compound which was used as crude for the next step (55 mg, quant.). LCMS (Method A): RT=1.54 min, ES+ 234 (M+H+). ES-232 (M−H+).

Step 11

(3E,3aR,8bS)-8,8-dimethyl-3-[(4-methyl-5-oxo-2H-furan-2-yl)oxymethylene]-3a,4,5,6,7,8b-hexahydro-1H-indeno[1,2-b]pyrrol-2-one (P1)

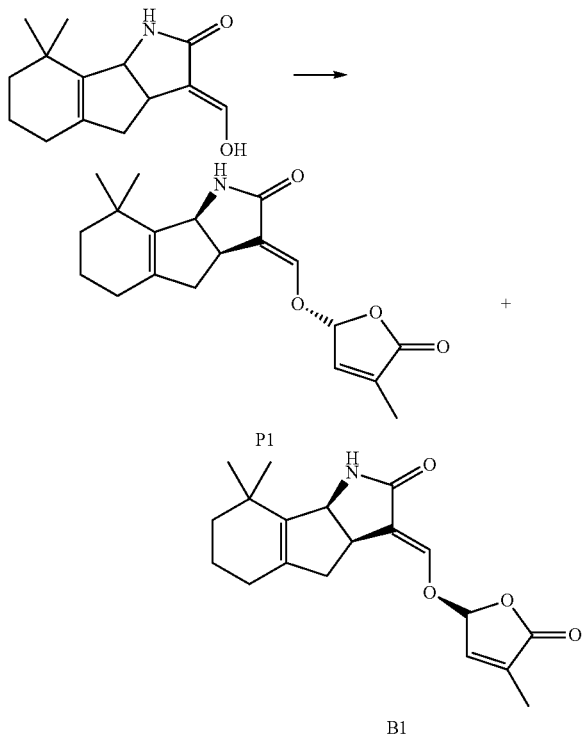

To a solution of (3E)-3-(hydroxymethylene)-8,8-dimethyl-3a,4,5,6,7,8b-hexahydro-1H-indeno[1,2-b]pyrrol-2-one (55 mg, 0.23 mmol) in DMF (2 mL) was added at 0° C. potassium tert butoxide (35 mg, 0.283 mmol). After 30 min, bromobutenolide (54 mg, 0.30 mmol, prepared according to Johnson & all, J.C.S. Perkin I, 1981, 1734-1743) in dichloromethane (0.5 mL) was added and the solution was stirred for 1 h. Water was added to the reaction mixture and the solution was extracted with ethyl acetate (3*15 mL), washed with brine (3*15 mL), dried and concentrated. The residue was purified by flash chromatography (CyH/EA, 1/1 to 1/4) to give a diastereoisomer P1 as the less polar isomer and B1 as the more polar isomer.

P1: $^1$H NMR (400 MHz, CDCl$_3$) δ ppm 7.22 (1H, d, J=2.6 Hz), 6.91 (1H, t, J=1.5 Hz), 6.11 (1H, t, J=1.5 Hz), 5.96 (1H, br. S), 4.61 (1H, d, J=7.7 Hz), 3.59 (1H, ddq, J=9.9, 7.7, 2.3 Hz), 2.71 (1H, dd, J=16.9, 9.9 Hz), 2.25-2.37 (1H, m), 2.02 (3H, t, J=1.5 Hz), 1.86-1.96 (2H, m), 1.58-1.68 (2H, m), 1.36-1.49 (2H, m), 1.06 (3H, s), 1.05 (3H, s). LCMS (Method B): RT=0.94 min, ES+ 330 (M+H+).

B1: $^1$H NMR (400 MHz, CDCl$_3$) δ ppm 7.22 (1H, d, J=2.6 Hz), 6.91 (1H, t, J=1.5 Hz), 6.11-5.96 (2H, m), 4.59 (1H, d, J=7.7 Hz), 3.59 (1H, ddq, J=9.9, 7.7, 2.3 Hz), 2.71 (1H, dd, J=16.9, 9.9 Hz), 2.25-2.37 (1H, m), 2.01 (3H, t, J=1.5 Hz), 1.86-1.96 (2H, m), 1.58-1.69 (2H, m), 1.36-1.50 (2H, m), 1.06 (3H, s), 1.05 (3H, s). LCMS (Method B): RT=0.93 min, ES+ 330 (M+H+).

(3E,3aR,8bS)-8,8-dimethyl-3-[(4-methyl-5-oxo-2H-furan-2-yl)oxymethylene]-3a,4,5,6,7,8b-hexahydro-1H-indeno[1,2-b]pyrrol-2-one (P9)

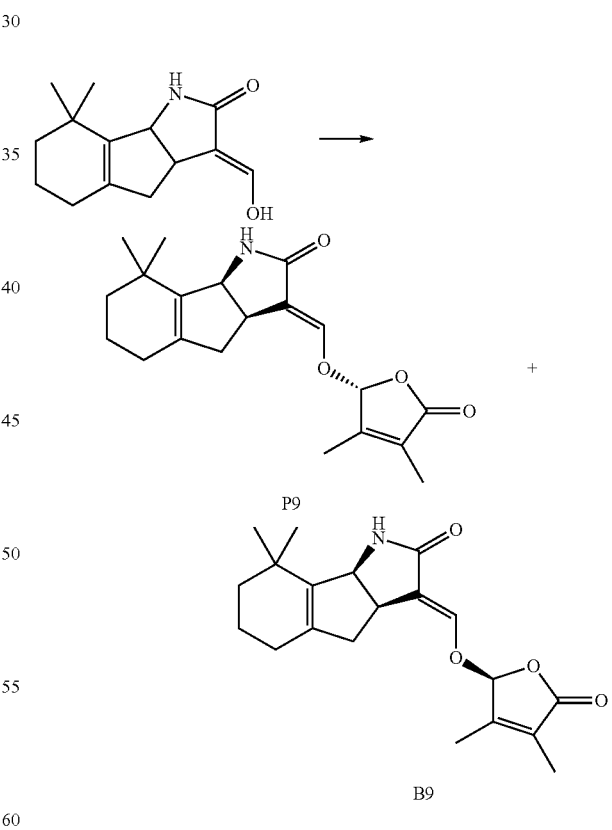

The compounds were prepared using a similar procedure starting from (3E)-3-(hydroxymethylene)-8,8-dimethyl-3a,4,5,6,7,8b-hexahydro-1H-indeno[1,2-b]pyrrol-2-one C1 and 2-chloro-3,4-dimethyl-2H-furan-5-one (Tetrahedron, 1978, 34, 1935-1942) and as a mixture of diastereoisomers P9 and B9. LCMS (Method C): RT=0.75 min, ES+ 344 (M+H$^+$).

Example 2

Synthesis of (3E,3aR,4aS,8bS)-3-[[(2R)-4-methyl-5-oxo-2H-furan-2-yl]oxymethylene]-1,3a,4,4a,5,6,7,8b-octahydroindeno[1,2-b]pyrrol-2-one

Step 1

Tert-butyl 2-(2-allylcyclohexylidene)acetate

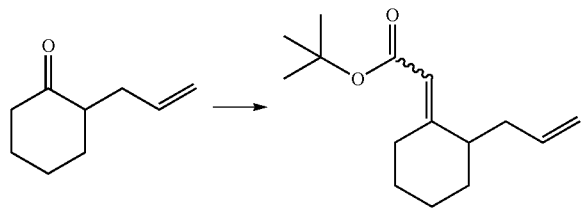

To a solution of diisopropylamine (6.60 mL, 46.6 mmol) in THF (200 mL) at −10° C., was added a solution 2.22M of n-butyllithium (20.4 mL, 44.4 mmol). The solution was stirred 15 min at −10° C., cooled down to −78° C. and tert-butyl 2-trimethylsilylacetate (9.7 mL, 44.4 mmol) in 1 mL of THF was added dropwise. The solution was stirred 15 min at −78° C., and 2-allylcyclohexanone (3.3 mL, 22.2 mmol) was added dropwise. The reaction mixture was stirred 1 h at −78° C. and 3 h at −25° C. It was then quenched with saturated NH$_4$Cl, extracted with ethylacetate, washed with brine, dried and concentrated. Purification by flash chromatography (cyclohexane) gave tert-butyl 2-(2-allylcyclohexylidene)acetate (5.06 g, 96%) as a colorless liquid. $^1$H NMR (400 MHz, CDCl$_3$) 5.62 (1H, m), 5.41 (1H, s), 4.89 (2H, m), 3.83 (1H, m), 2.16 (3H, m), 1.90 (1H, m), 1.73 (1H, m), 1.61 (1H, m), 1.47-1.22 (4H, m), 1.36 (9H, s).

tert-butyl 2-(2-allylcyclopentylidene)acetate

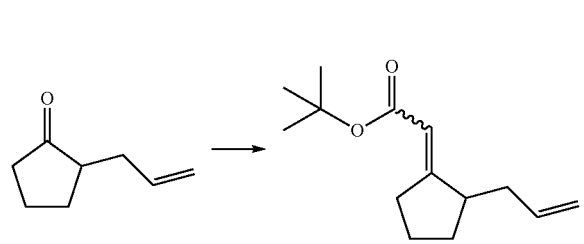

The compound was prepared using a similar procedure starting from 2-allylcyclopentanone. LCMS (Method C): RT=1.28 min; ES+ 167 (M−tBu+H$^+$).

Step 2

2-(2-allylcyclohexylidene)acetic acid

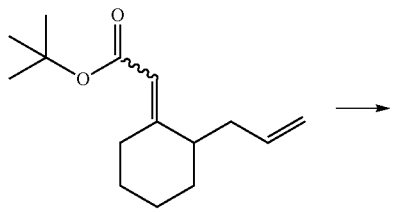

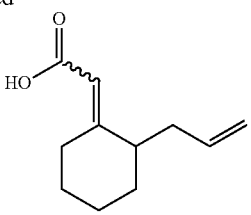

To a solution of tert-butyl 2-(2-allylcyclohexylidene)acetate (1.00 g, 4.230 mmol) in dichloromethane (40 mL) at room temperature was added trifluoroacetic acid (0.688 mL, 8.883 mmol) and the solution was stirred at room temperature overnight. The solvent was then evaporated and excess of trifluoroacetic acid was removed by co-evaporation with toluene, giving 2-(2-allylcyclohexylidene)acetic acid (768 mg, 100%) as a colorless oil; $^1$H NMR (400 MHz, CDCl$_3$) 5.59 (1H, m), 5.46 (1H, s), 4.82 (2H, m), 3.36 (1H, m), 2.19 (1H, m), 2.12 (2H, m), 1.93 (1H, m), 1.71 (1H, m), 1.61 (1H, m), 1.55 (1H, m), 1.47 (2H, m), 1.22 (1H, m).

2-(2-allylcyclopentylidene)acetic acid

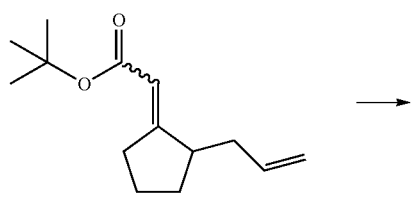

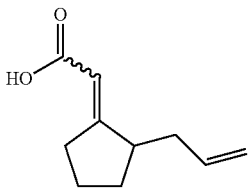

The compound was prepared using a similar procedure starting from tert-butyl 2-(2-allylcyclopentylidene)acetate. LCMS (Method C): RT=0.90 min; ES+ 167 (M+H+).

Step 3

1,2a,4,5,6,6a,7,7a-octahydrocyclobuta[a]inden-2-one

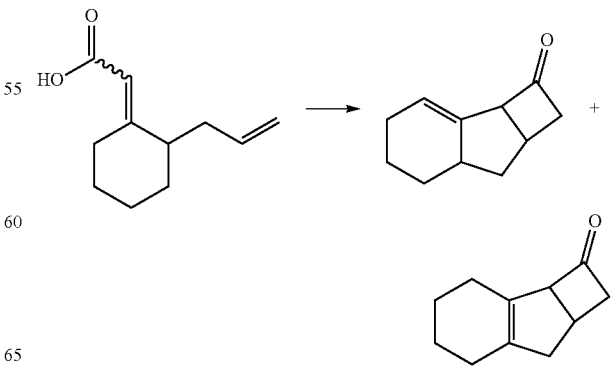

A solution of 2-(2-allylcyclohexylidene)acetic acid (800 mg, 4.44 mmol) in dichloromethane (200 mL) was added Ghosez reagent (5.77 mmol, 0.795 mL) at room temperature. The solution was stirred for 45 min until the acid chloride was formed. Then N,N-dimethylaminopyridine (55 mg, 0.45 mmol) was added and the solution was heated to reflux. A solution of triethylamine (8.9 mmol, 1.25 mL) in dichloromethane (3.75 mL) was added dropwise over 30 min. The solution was refluxed for another 1 h and solvent was distilled off. Purification by flash chromatography (pentane/Et$_2$O 95/5) gave 1,2a,4,5,6,6a,7,7a-octahydrocyclobuta[a]inden-2-one (600 mg, 83%) as a colourless liquid, with 20% of the tetrasubstituted regioisomere. $^1$H NMR (400 MHz, CDCl$_3$) 5.59 (1H, brs), 3.92 (1H, brs), 3.21 (1H, dddd), 2.92 (1H, m), 2.73 (1H, m), 2.51 (1H, m), 2.04 (4H, m), 1.79 (1H, m), 1.48 (2H, m), 1.05 (1H, m).

1,2a,4,5,5a,6,6a-hexahydrocyclobuta[a]pentalen-2-one

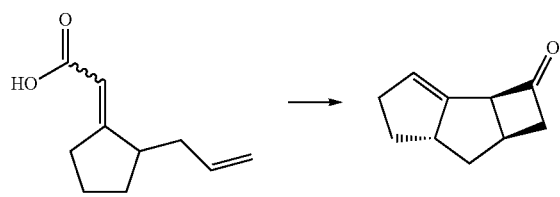

The compound was prepared using a similar procedure starting from 2-(2-allylcyclopentylidene)acetic acid as a single regioisomer. LCMS (Method C): RT=1.01 min; ES+ 149 (M+H$^+$).

Step 4

3,3a,4,4a,5,6,7,8b-octahydro-1H-indeno[1,2-b]pyrrol-2-one

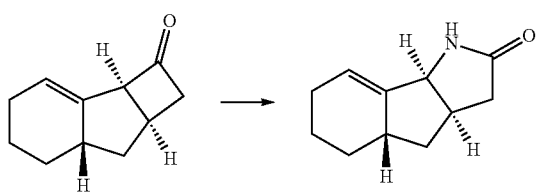 [SMILES: O=C1C[C@H]2C[C@@H]3CCCC=C3[C@@H]12 ; O=C1C[C@H]2C[C@@H]3CCCC=C3[C@H]2N1]

To a solution of 1,2a,4,5,6,6a,7,7a-octahydrocyclobuta[a]inden-2-one (3.70 mmol, 0.600 g) in dichloromethane (40 mL) was added O-mesitylenesulfonylhydroxylamine (4.44 mmol, 1.47 g) and the solution was stirred at room temperature for 3 h. The mixture was washed with sat. NaHCO$_3$, dried and concentrated. Purification by flash chromatography (ethyl acetate) gave the lactam (562 mg, 85%) as a yellow oil, with 20% of the tetrasubstituted regioisomere. $^1$H NMR (400 MHz, MeOD) 5.53 (1H, d), 4.30 (1H, d), 2.97 (1H, m), 2.63 (2H, m), 2.50 (1H, m), 2.04 (4H, m), 1.83 (1H, m), 1.68 (1H, m), 1.51 (1H, m), 1.39 (1H, m), 1.02 (1H, m).); LCMS (Method B): RT=0.76 min; ES+ 178 (M+H$^+$).

3,3a,4,5,6,7,8,8b-octahydro-1H-indeno[1,2-b]pyrrol-2-one

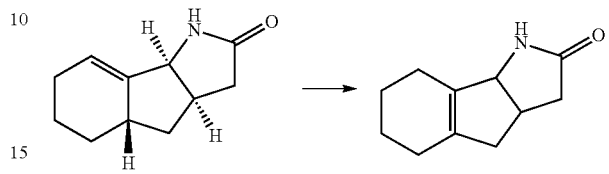

To a solution of 3,3a,4,4a,5,6,7,8b-octahydro-1H-indeno[1,2-b]pyrrol-2-one (600 mg, 3.38 mmol) in chloroform-d-3 (4 mL) under argon was added triflic acid (0.152 mL) and the solution was stirred 4 h at 40° C. The solution was cooled down and passed through celite, washed with dichloromethane and evaporated. Purification by flash chromatography (ethyl acetate) gave 3,3a,4,5,6,7,8,8b-octahydro-1H-indeno[1,2-b]pyrrol-2-one (322 mg, 53%) as an orange oil. LCMS (Method B): 0.76 min; ES+ 178 (M+H$^+$).

(3aR,4aS,7bS)-1,3,3a,4,4a,5,6,7b-octahydropentaleno[1,2-b]pyrrol-2-one

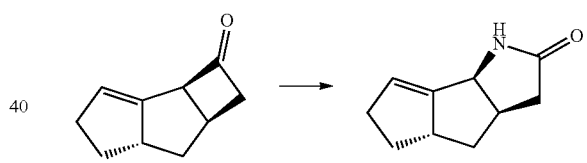

The compound was prepared using a similar procedure starting from 1,2a,4,5,5a,6,6a-hexahydrocyclobuta[a]pentalen-2-one. LCMS (Method C): RT=0.69 min; ES+ 164 (M+H$^+$).

1,3,3a,4,4a,5,6,7,7a,7b-decahydropentaleno[1,2-b]pyrrol-2-one

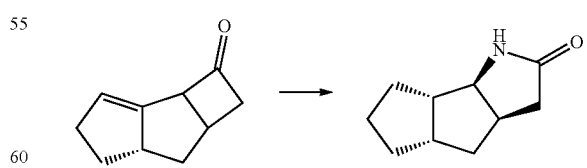

The compound was prepared using a similar procedure starting from 1,2a,4,5,5a,6,6a-hexahydrocyclobuta[a]pentalen-2-one and using 3 equivalents of O-mesitylenesulfonylhydroxylamine, leaving the reaction overnight. LCMS (Method C): RT=0.71 min; ES+ 166 (M+H$^+$).

Step 5 tert-butyl-2-oxo-3,3a,4,4a,5,6,7,8b-octahydroindeno
[1,2-b]pyrrole-1-carboxylate

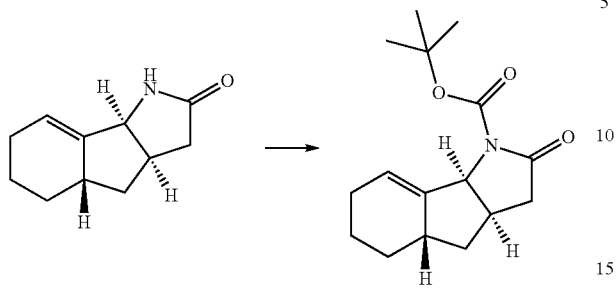

To a solution of 3,3a,4,4a,5,6,7,8b-octahydro-1H-indeno
[1,2-b]pyrrol-2-one (547 mg, 3.08 mmol) in CH$_2$Cl$_2$ (30 mL)
was added di-tert-butyl dicarbonate (2.1 mL, 9.25 mmol),
Et$_3$N (1.3 mL, 9.25 mmol) and N,N-dimethylaminopyridine
(38 mg, 0.31 mmol). The solution was stirred for 20 h, poured
into water and extracted with CH$_2$Cl$_2$. The combined organic
layers were washed with brine, dried, concentrated and crude
residue was purified by flash chromatography (cyclohexane/
ethyl acetate 3/1) to give the desired compound as a yellow oil
(403 mg, 47%), with 20% of the tetrasubstituted regioisomer;
$^1$H NMR (400 MHz, CDCl$_3$) 6.01 (1H, brs), 4.81 (1H, d), 2.78
(2H, m), 2.44 (1H, m), 2.27 (1H, m), 2.02 (4H, m), 1.81 (2H,
m), 1.51 (9H, s), 1.32 (1H, m), 0.99 (1H, m); LCMS (Method
B): RT=1.09 min; ES+577 (2M+Na$^+$).

tert-butyl-2-oxo-(3aR,4aS,7bS),3,3a,4,4a,5,6,7b-
octahydropentaleno[1,2-b]pyrrol-1-carboxylate

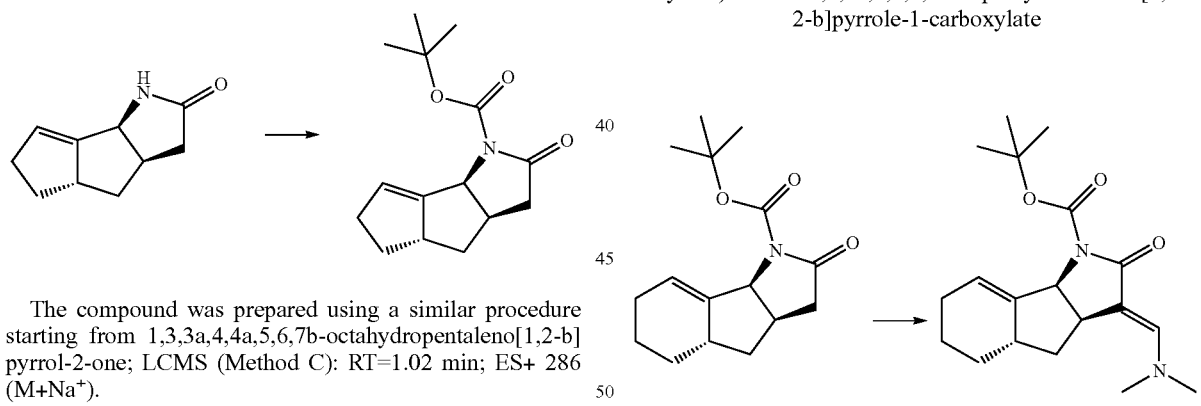

The compound was prepared using a similar procedure
starting from 1,3,3a,4,4a,5,6,7b-octahydropentaleno[1,2-b]
pyrrol-2-one; LCMS (Method C): RT=1.02 min; ES+ 286
(M+Na$^+$).

tert-butyl 2-oxo-3a,4,4a,5,6,7,7a,7b-octahydro-3H-
pentaleno[1,2-b]pyrrole-1-carboxylate

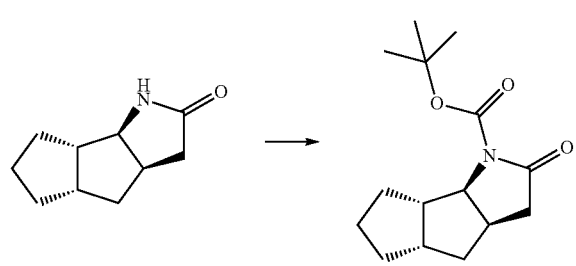 [SMILES: O=C1C[C@H]2C[C@@H]3CCC[C@@H]3[C@H]2N1 ; CC(C)(C)OC(=O)N1C(=O)C[C@H]2C[C@@H]3CCC[C@@H]3[C@H]21]

The compound was prepared using a similar procedure
starting from 1,3,3a,4,4a,5,6,7,7a,7b-decahydropentaleno[1,
2-b]pyrrol-2-one; LCMS (Method B): RT=1.04 min; ES+
288 (M+Na$^+$).

tert-butyl (3aR,8bS)-2-oxo-3,3a,4,5,6,7,8,8b-octahy-
droindeno[1,2-b]pyrrole-1-carboxylate

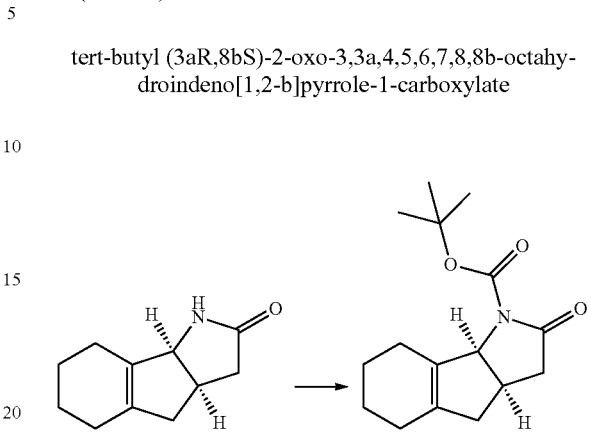

The compound was prepared using a similar procedure
starting from 3,3a,4,5,6,7,8,8b-octahydro-1H-indeno[1,2-b]
pyrrol-2-one; LCMS (Method C): RT=1.09 min; ES+ 577
(2M+Na$^+$).

Step 6 tert-butyl (3E,3aR,4aS,8bS)-3-(dimethylaminometh-
ylene)-2-oxo-3a,4,4a,5,6,7,8b-heptahydro-indeno[1,
2-b]pyrrole-1-carboxylate To a solution of tert-butyl 2-oxo-3,3a,4,4a,5,6,7,8b-oc-
tahydroindeno[1,2-b]pyrrole-1-carboxylate (349 mg, 1.26
mmol) in toluene (13 mL) was added tert-butoxybis(dimethy-
lamino)methane (0.78 mL, 3.77 mmol). The solution was
heated for 2 h at 110° C. It was then cooled to room tempera-
ture, poured into water (20 mL), diluted with ethyl acetate (20
mL), and extracted 3 times. The combined organic layers
were washed with brine, dried, concentrated and purified by
flash chromatography (ethyl acetate) giving the desired com-
pound as an orange oil (392 mg, 89%), with 20% of the
tetrasubstituted regioisomer; $^1$H NMR (400 MHz, CDCl$_3$)
7.11 (1H, s), 5.97 (1H, m), 4.68 (1H, d), 3.52 (1H, m), 3.02
(6H, s), 2.39 (1H, m), 1.98 (4H, m), 1.71 (1H, m), 1.57 (1H,
m), 1.53 (9H, s), 1.40 (1H, m), 0.96 (1H, m); LCMS (Method
B): RT=1.10 min; ES+ 687 (2M+Na$^+$).

tert-butyl (3E,3aR,4aS,7bS)-3-(dimethylaminometh-
ylene)-2-oxo-3a,4,4a,5,6,7b-hexahydropentaleno[1,
2-b]pyrrole-1-carboxylate

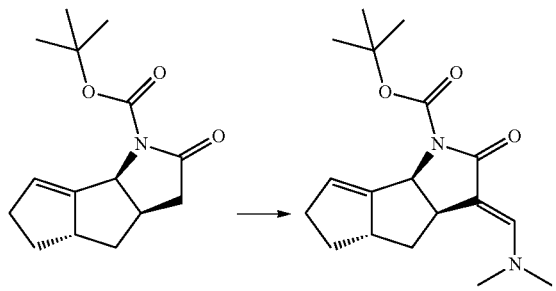 [SMILES: CC(C)(C)OC(=O)N1C(=O)C[C@H]2C[C@@H]3CCC=C3[C@H]21 ; CN(C)/C=C1/C(=O)N(C(=O)OC(C)(C)C)[C@@H]2C3=CCC[C@H]3C[C@H]12]

The compound was prepared using a similar procedure starting from tert-butyl-2-oxo-3,3a,4,4a,5,6,7b-octahydro-pentaleno[1,2-b]pyrrol-1-carboxylate; ¹H NMR (400 MHz, CDCl₃) 7.06 (1H, s), 5.57 (1H, m), 4.55 (1H, d), 3.78 (1H, t), 3.05 (1H, m), 3.02 (6H, s), 2.58 (1H, m), 2.45 (1H, m), 2.01 (1H, m), 1.96 (1H, m), 1.53 (9H, s), 1.40 (2H, m).

tert-butyl (3E,3aR,4aS,7aS,7bR)-3-(dimethylami-
nomethylene)-2-oxo-3a,4,4a,5,6,7,7a,7b-octahydro-
pentaleno[1,2-b]pyrrole-1-carboxylate

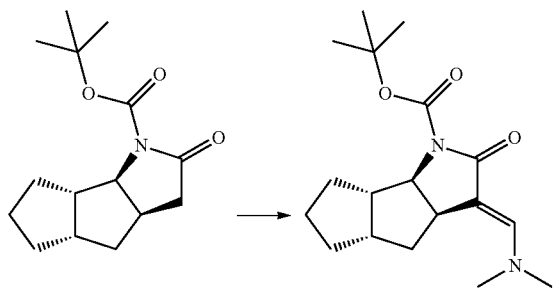 [SMILES: CC(C)(C)OC(=O)N1C(=O)C[C@H]2C[C@@H]3CCC[C@@H]3[C@H]21 ; CN(C)/C=C1/C(=O)N(C(=O)OC(C)(C)C)[C@@H]2[C@H]3CCC[C@H]3C[C@H]12]

The compound was prepared using a similar procedure starting from tert-butyl 2-oxo-3a,4,4a,5,6,7,7a,7b-octahydro-3H-pentaleno[1,2-b]pyrrole-1-carboxylate. LCMS (Method B): RT=1.08 min; ES+ 321 (M+H⁺).

tert-butyl (3E,3aR,8bS)-3-(dimethylaminomethyl-
ene)-2-oxo-4,5,6,7,8,8b-hexahydro-3aH-indeno[1,2-
b]pyrrole-1-carboxylate

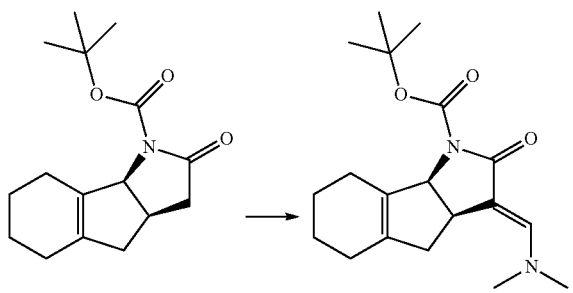 [SMILES: CC(C)(C)OC(=O)N1C(=O)C[C@H]2CC3=C(CCCC3)[C@H]21 ; CN(C)/C=C1/C(=O)N(C(=O)OC(C)(C)C)[C@@H]2C3=C(CCCC3)C[C@H]12]

The compound was prepared using a similar procedure starting from tert-butyl 2-oxo-3,3a,4,5,6,7,8,8b-octahydroin-deno[1,2-b]pyrrole-1-carboxylate. LCMS (Method B): RT=1.11 min; ES+ 333 (M+H⁺).

Step 7 tert-butyl (3Z,3aR,4aS,8bS)-3-(hydroxymethylene)-
2-oxo-4,4a,5,6,7,8b-hexahydro-3aH-indeno[1,2-b]
pyrrole-1-carboxylate C2

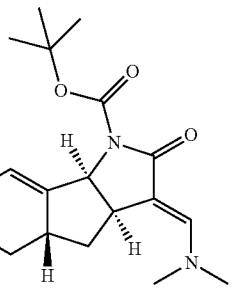

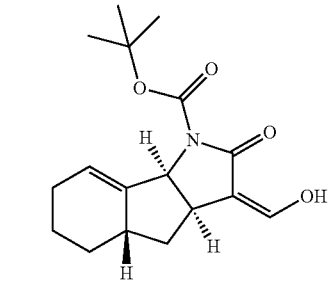

A solution of tert-butyl (3E,3aR,4aS,8bS)-3-(dimethylaminomethylene)-2-oxo-4,4-a,5,6,7,8b-hexahydro-3aH-indeno[1,2-b]pyrrole-1-carboxylate (380 mg, 1.09 mmol) in dioxane (10 mL) was stirred with hydrochloric acid (2 M, 1.63 mL, 3.27 mmol) for 1.5 h at room temperature. The solution was diluted with ethyl acetate, washed with water and brine, dried, concentrated giving the desired compound as a yellow oil (324 mg, 97%), with 20% of the tetrasubstituted regioisomer; ¹H NMR (400 MHz, DMSO-d6) 10.79 (1H, d), 7.38 (1H, d), 5.94 (1H, brs), 4.69 (1H, d), 2.17 (2H, m), 1.98 (4H, m), 1.69 (1H, m), 1.46 (9H, s), 1.18 (2H, m), 0-91 (1H, m). LCMS (Method C): RT=1.04 min; ES+ 328 (M+Na⁺).

tert-butyl (3E,3aR,4aS,7bS)-3-(hydroxymethylene)-
2-oxo-3a,4,4a,5,6,7b-hexahydropentaleno[1,2-b]
pyrrole-1-carboxylate C3

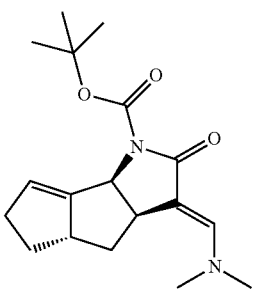

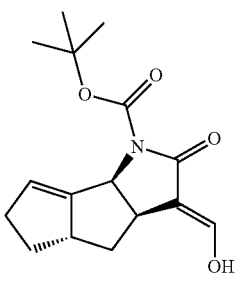

The compound was prepared using a similar procedure starting from tert-butyl 3-(dimethylaminomethylene)-2-oxo-3a,4,4a,5,6,7b-hexahydropentaleno[1,2-b]pyrrole-1-carboxylate; LCMS (Method C): RT=0.99 min; ES+ 314 (M+Na⁺).

tert-butyl (3E,3aR,4aS,7aS,7bR)-3-(hydroxymethylene)-2-oxo-3a,4,4a,5,6,7,7a,7b-octahydropentaleno[1,2-b]pyrrole-1-carboxylate C4

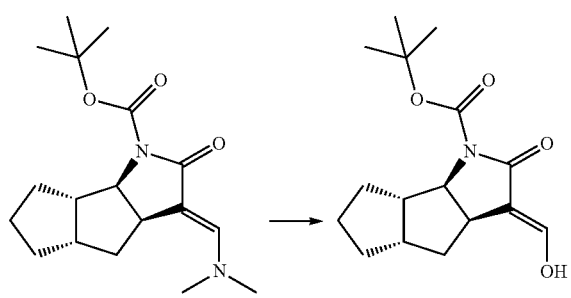 [SMILES: CN(C)/C=C1/C(=O)N(C(=O)OC(C)(C)C)[C@@H]2[C@H]3CCC[C@H]3C[C@H]12 ; CC(C)(C)OC(=O)N1C(=O)/C(=C/O)[C@H]2C[C@@H]3CCC[C@@H]3[C@H]21]

The compound was prepared using a similar procedure starting from tert-butyl (3E,3aR,4aS,7aS,7bR)-3-(dimethylaminomethylene)-2-oxo-3a,4,4a,5,6,7,7a,7b-octahydropentaleno[1,2-b]pyrrole-1-carboxylate. LCMS (Method B): RT=1.02 min; ES− 292 (M−H⁺).

tert-butyl (3Z,3aR,8bS)-3-(hydroxymethylene)-2-oxo-4,5,6,7,8,8b-hexahydro-3aH-indeno[1,2-b]pyrrole-1-carboxylate C5

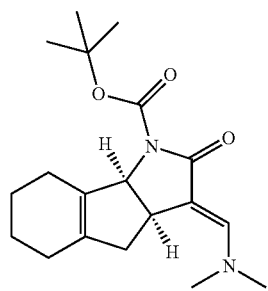

The compound was prepared using a similar procedure starting from tert-butyl tert-butyl (3E,3aR,8bS)-3-(dimethylaminomethylene)-2-oxo-4,5,6,7,8,8b-hexahydro- 3aH-indeno[1,2-b]pyrrole-1-carboxylate. LCMS (Method B): RT=1.06 min; ES+ 328 (M+Na⁺).

Step 8 tert-butyl (3E,3aR,4aS,8bS)-3-[(4-methyl-5-oxo-2H-furan-2-yl)oxymethylene]-2-oxo-4,4-a,5,6,7,8b-hexahydro-3aH-indeno[1,2-b]pyrrole-1-carboxylate P3 and B3

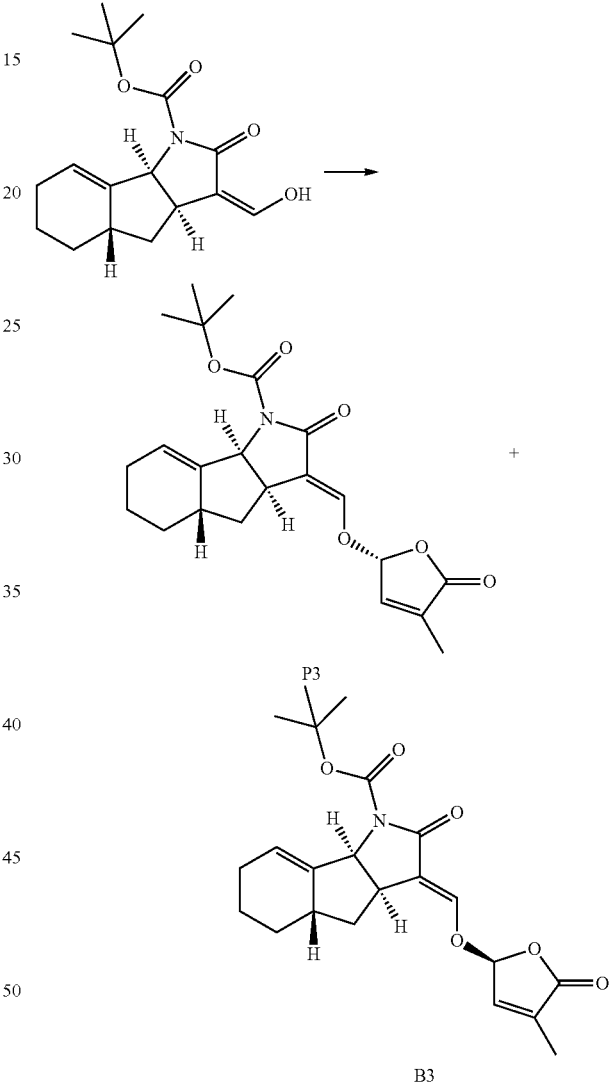

To a solution of tert-butyl (3Z,3aR,4aS,8bS)-3-(hydroxymethylene)-2-oxo-4,4-a,5,6,7,8b-hexahydro-3aH-indeno[1,2-b]pyrrole-1-carboxylate (324 mg, 1.06 mmol) in THF (10 mL) cooled to 0° C. was added potassium tert-butoxide (1.59 mmol, 0.184 g) and 18-crown-6 (1.59 mmol, 0.420 g). After 10 min, 2-chloro-4-methyl-2H-furan-5-one (1.27 mmol, 0.169 g) in 1 mL of THF was added and the solution was stirred for 1 h. Water was added and the aqueous layer was extracted with ethyl acetate (4*20 mL). The combined organic layers were dried and concentrated. The product was purified by flash chromatography (30% ethyl acetate to 50% ethyl acetate in cyclohexane) to give the desired product as two isomers, each of them containing 20% of the tetrasubstituted regioisomer from step 3:

less polar diastereoisomer: tert-butyl (3E,3aR,4aS,8bS)-3-[[(2R)-4-methyl-5-oxo-2H-furan-2-yl]oxymethylene]-2-oxo-4,4a,5,6,7,8b-hexahydro-3aH-indeno[1,2-b]pyrrole-1-carboxylate P3 (83 mg, 19%). $^1$H NMR (400 MHz, CDCl$_3$) 7.49 (1H, d), 6.91 (1H, s), 6.14 (1H, s), 6.02 (1H, brs), 4.79 (1H, d), 3.34 (1H, dd), 2.28 (1H, m), 2.17 (1H, m), 2.04 (2H, m), 2.01 (3H, s), 1.75 (1H, m), 1.60 (9H, s), 1.40 (1H, m), 1.28 (1H, m), 0.96 (1H, m). LCMS (Method B): RT=1.13 min; ES+ 402 (M+H$^+$).

more polar diastereoisomer: tert-butyl (3E,3aR,4aS,8bS)-3-[[(2S)-4-methyl-5-oxo-2H-furan-2-yl]oxymethylene]-2-oxo-4,4a,5,6,7,8b-hexahydro-3aH-indeno[1,2-b]pyrrole-1-carboxylate B3 (79 mg, 18%). $^1$H NMR (400 MHz, CDCl$_3$) 7.49 (1H, d), 6.91 (1H, s), 6.12 (1H, s), 6.01 (1H, brs), 4.79 (1H, d), 3.32 (1H, dd), 2.28 (1H, m), 2.14 (1H, dd), 2.04 (3H, m), 2.01 (3H, s), 1.72 (1H, m), 1.60 (9H, s), 1.40 (1H, m), 1.25 (1H, m), 0.92 (1H, m). LCMS (method B): RT=1.14 min; ES+ 402 (M+H$^+$).

Tert-butyl (3E,3aR,4aS,7bS)-3-[[4-methyl-5-oxo-2H-furan-2-yl]oxymethylene]-2-oxo-3a,4,4a,5,6,7b-hexahydropentaleno[1,2-b]pyrrole-1-carboxylate P5

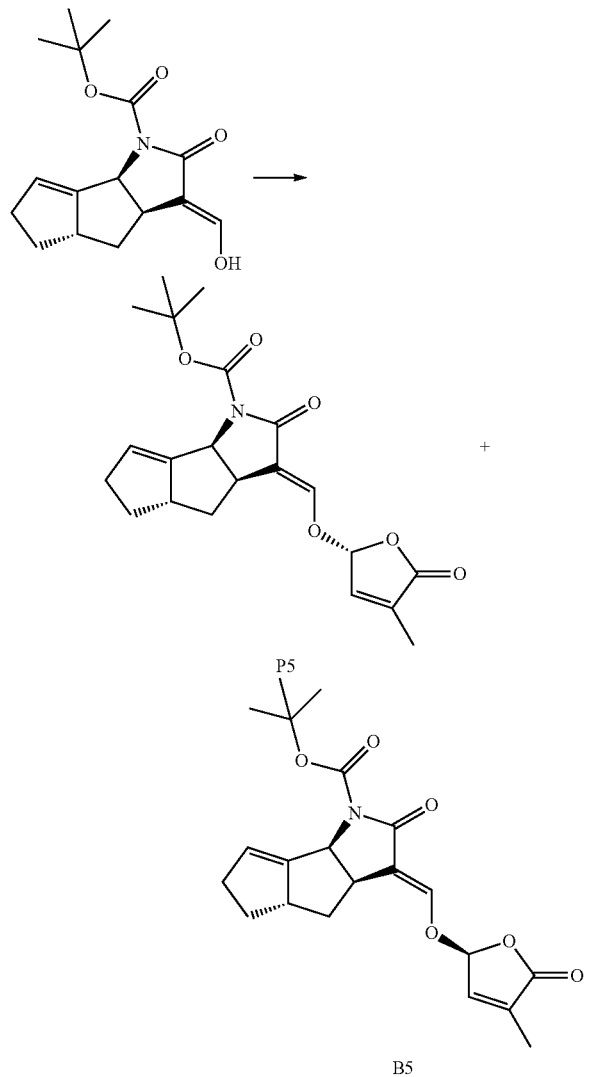

The compound was prepared using a similar procedure starting from tert-butyl 3-(hydroxymethylene)-2-oxo-3a,4,4a,5,6,7b-hexahydropentaleno[1,2-b]pyrrole-1-carboxylate as a mixture of isomers P5 and B5: LCMS (Method C): RT=1.09 min; ES+ 797 (2M+Na$^+$).

tert-butyl (3E,3aR,4aS,7aS,7bR)-3-[[4-methyl-5-oxo-2H-furan-2-yl]oxymethylene]-2-oxo-3a,4,4a,5,6,7,7a,7b-octahydropentaleno[1,2-b]pyrrole-1-carboxylate P7 and B7

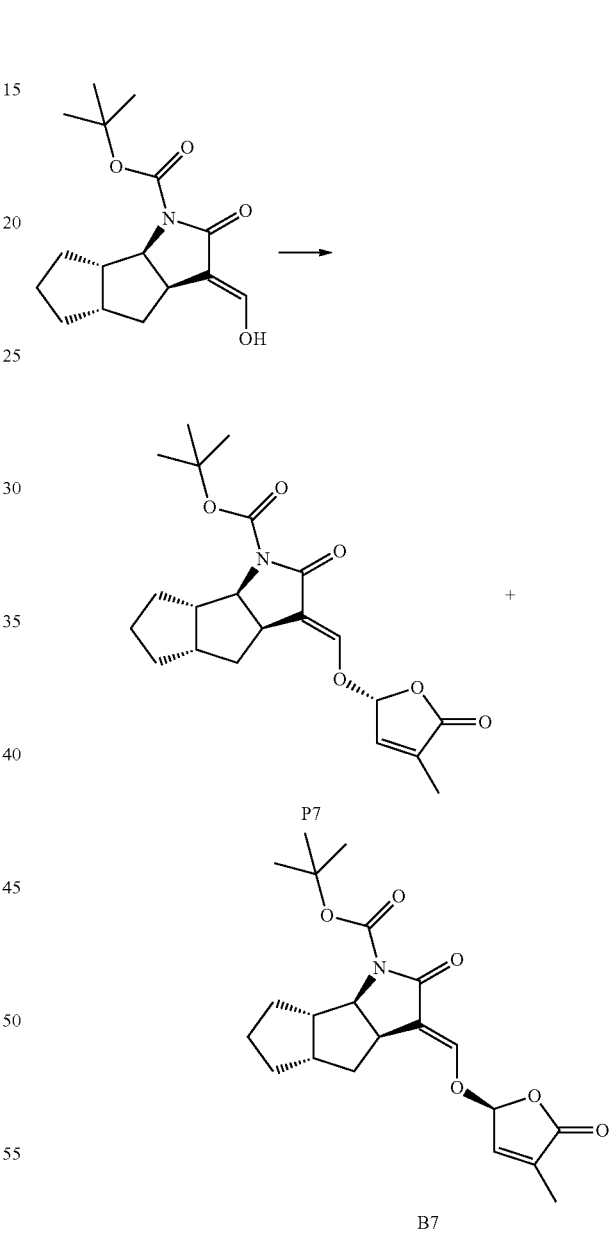

The compound was prepared using a similar procedure starting from tert-butyl (3E,3aR,4aS,7aS,7bR)-3-(hydroxymethylene)-2-oxo-3a,4,4a,5,6,7,7a,7b-octahydropentaleno[1,2-b]pyrrole-1-carboxylate as a mixture of isomers P7 and B7. LCMS (Method B): RT=1.12 min; ES+ 390 (M+H$^+$).

tert-butyl (3E,3aR,8bS)-3-[[(2R)-4-methyl-5-oxo-2H-furan-2-yl]oxymethylene]-2-oxo-4,5,6,7,8,8b-hexahydro-3aH-indeno[1,2-b]pyrrole-1-carboxylate P10 and B10

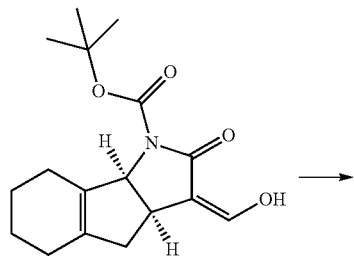

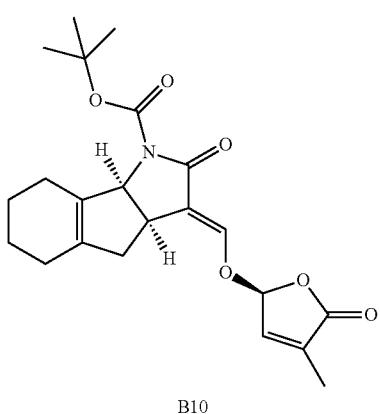

P10

+

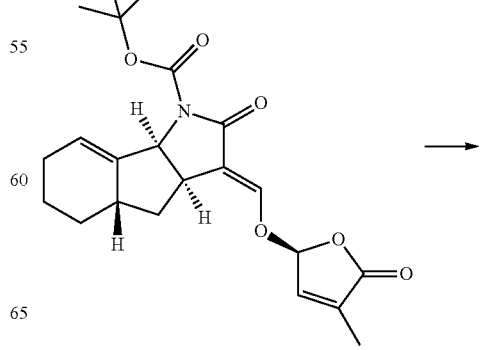

B10

The compound was prepared using a similar procedure starting from tert-butyl (3Z,3aR,8bS)-3-(hydroxymethylene)-2-oxo-4,5,6,7,8,8b-hexahydro-3aH-indeno[1,2-b]pyrrole-1-carboxylate as a mixture of isomers P10 and B10. LCMS (Method B): RT=1.15 min; ES+465 (M+MeCN+Na+).

Step 9

(3E,3aR,4aS,8bS)-3-[[(2R)-4-methyl-5-oxo-2H-furan-2-yl]oxymethylene]-1,3a,4,4a,5,6,7,8b-octahydroindeno[1,2-b]pyrrol-2-one P2

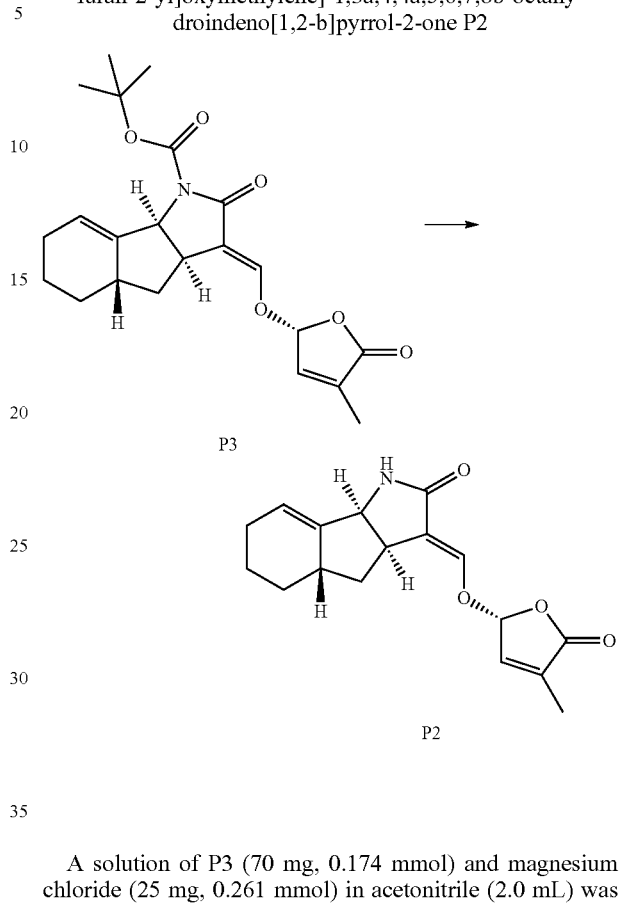

P3

P2

A solution of P3 (70 mg, 0.174 mmol) and magnesium chloride (25 mg, 0.261 mmol) in acetonitrile (2.0 mL) was stirred overnight at 40° C. The solution was diluted with ethyl acetate and filtered and the filtrate was evaporated. The product was purified by flash chromatography (ethyl acetate) to give the desired product P2 (36 mg, 68%), with 20% of the tetrasubstituted isomere. 1H NMR (400 MHz, CDCl$_3$) 7.21 (1H, brs), 6.92 (1H, brs), 6.11 (1H, brs), 5.70 (1H, brs), 4.26 (1H, d), 3.49 (1H, dd), 2.37 (1H, m), 2.11 (1H, m), 2.01 (3H, s), 1.99 (2H, m), 1.76 (1H, m), 1.62 (1H, m), 1.38 (2H, m), 0.96 (1H, m). LCMS (Method B): RT=0.90 min; ES+ 302 (M+H+).

(3E,3aR,4aS,8bS)-3-[[(2S)-4-methyl-5-oxo-2H-furan-2-yl]oxymethylene]-1,3a,4,4a,5,6,7,8b-octahydroindeno[1,2-b]pyrrol-2-one B2

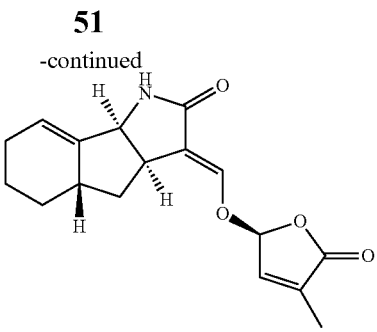

The title compound was prepared using a similar procedure from B3. (Method B): 0.89 min; ES+ 302 (M+H⁺).

3E 3-[[4-methyl-5-oxo-2H-furan-2-yl]oxymethylene]-1,3a,4,4a,5,6,7b-hexahydropentaleno[1,2-b]pyrrol-2-one P4

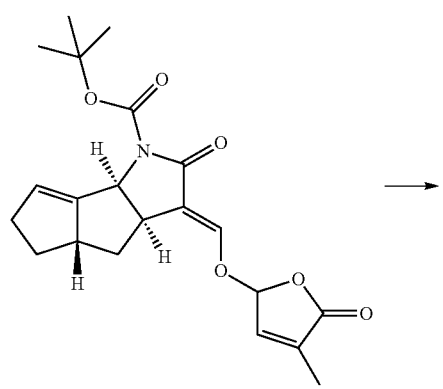

P5 + B5

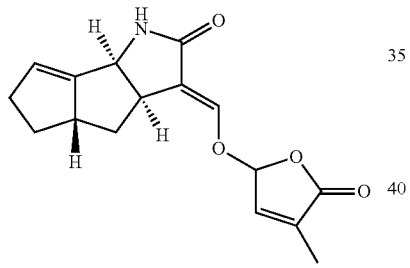

P4 + B4

The title compound was prepared using a similar procedure from the 1:1 mixture of P5 and B5. LCMS (Method C): RT=0.85 min; ES+ 288 (M+H⁺).

(3E,3aR,4aS,7aS,7bR)-3-[(4-methyl-5-oxo-2H-furan-2-yl)oxymethylene]-3a,4,4a,5,6,7,7a,7b-octahydro-1H-pentaleno[1,2-b]pyrrol-2-one P8 and B8

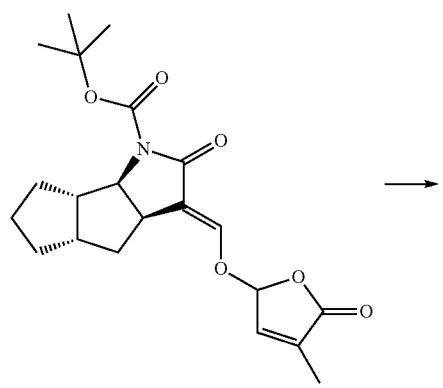

P7 + B7

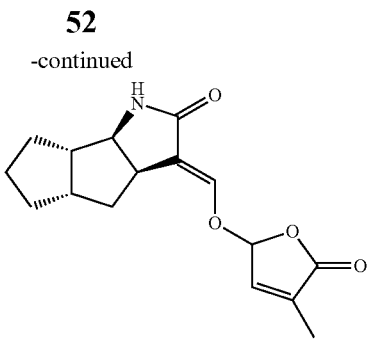

P8 + B8

The title compound was prepared using a similar procedure from the 1:1 mixture of P7 and B7. LCMS (Method C): RT=0.85 min; ES+ 290 (M+H⁺).

(3E,3aR,4aS,7aS,7bR)-3-[(4-methyl-5-oxo-2H-furan-2-yl)oxymethylene]-3a,4,4a,5,6,7,7a,7b-octahydro-1H-pentaleno[1,2-b]pyrrol-2-one P11 and B11

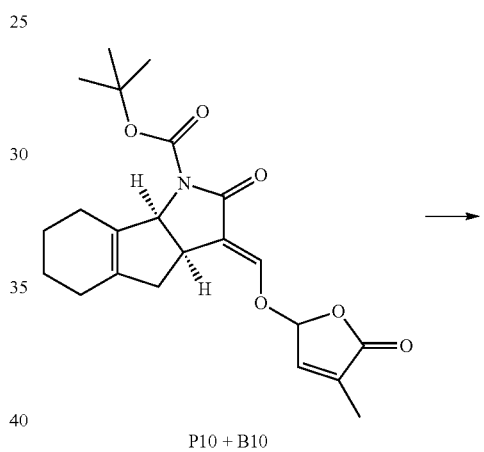

P10 + B10

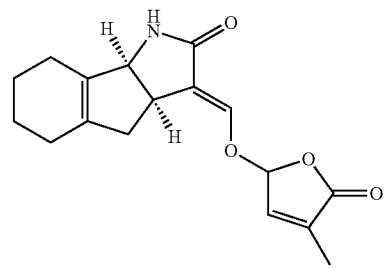

P11 + B11

The compound was prepared using a similar procedure from the 1:1 mixture of tert-butyl (3E,3aR,8bS)-3-[[(2R)-4-methyl-5-oxo-2H-furan-2-yl]oxymethylene]-2-oxo-4,5,6,7, 8,8b-hexahydro-3aH-indeno[1,2-b]pyrrole-1-carboxylate P10 and B10. LCMS (Method C): RT=0.90 min; ES+ 290 (M+H⁺).

Step 10

(3E,3aR,4aS,7bS) 1-acetyl-3-[(4-methyl-5-oxo-2H-furan-2-yl)oxymethylene]-3a,4,4a,5,6,7b-hexahydro-pentaleno[1,2-b]pyrrol-2-one P6

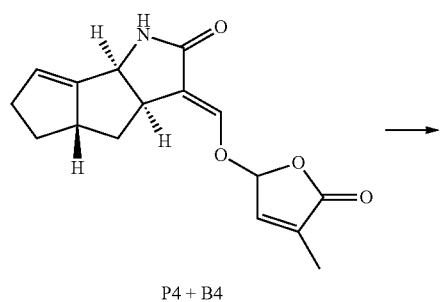

P4 + B4

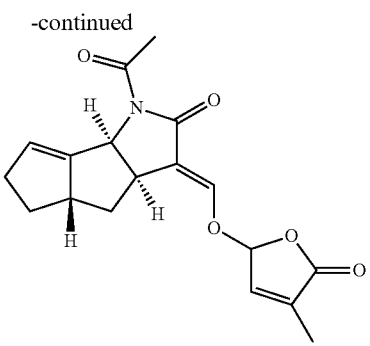

P6 + B6

3E 3-[[4-methyl-5-oxo-2H-furan-2-yl]oxymethylene]-1,3a,4,4a,5,6,7b-hexahydropentaleno[1,2-b]pyrrol-2-one P4 and B4 and N,N-dimethylaminopyridine (0.9 mg, 0.007 mmol) were dissolved in dichloromethane (1 mL) and triethylamine (0.019 mL, 0.14 mmol) was added followed by acetic anhydride (0.010 mL, 0.11 mmol) dropwise and the reaction mixture was stirred over night at room temperature. The reaction mixture was poured into sat. ammonium chloride solution and extracted with ethyl acetate, washed with brine, dried over MgSO₄ and the solvent was evaporated. The product was purified by flash chromatography (1:1 ethyl acetate and cyclohexane) to give P6 and B6 (4 mg, 35%). LCMS (Method C): RT=0.97 min; ES+ 330 (M+H⁺).

TABLE A

Compounds of Formula (I), less polar diastereoisomer
($R_2 = R_3 = R_4 = R_5 = R_8 = H$, $A_4 = CH_2$, $R_6 = Me$, $W = O$)

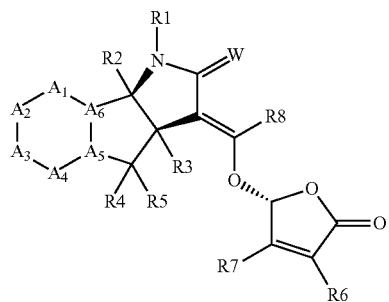

| Ex. | R1 | $A_1$ | $A_2$ | $A_3$ | $A_5$ | $A_6$ | $R_7$ | LCMS | Retention | Mass |
|---|---|---|---|---|---|---|---|---|---|---|
| P1 (1.02) | H | C(CH₃)₂ | CH₂ | CH₂ | C | C | H | B | 0.94 | 330 (M + H⁺) |
| P2 | H | CH | CH₂ | CH₂ | CH | C | H | B | 0.90 | 302 (M + H⁺) |
| P3 | Boc | CH | CH₂ | CH₂ | CH | C | H | B | 1.13 | 402 (M + H⁺) |
| P4* | H | CH |  | CH₂ | CH | C | H | C | 0.85 | 288 (M + H⁺) |
| P5* | Boc | CH |  | CH₂ | CH | C | H | C | 1.09 | 797 (2M + Na⁺) |
| P6* | Ac | CH |  | CH₂ | CH | C | H | C | 0.97 | 330 (M + H⁺) |
| P7* | Boc | CH₂ |  | CH₂ | CH | CH | H | C | 1.12 | 390 (M + H⁺) |
| P8* | H | CH₂ |  | CH₂ | CH | CH | H | B | 0.85 | 290 (M + H⁺) |
| P9* | H | C(CH₃)₂ | CH₂ | CH₂ | C | C | Me | C | 0.75 | 344 (M + H⁺) |
| P10* | Boc | CH₂ | CH₂ | CH₂ | C | C | H | B | 1.15 | 465 (M + MeCN + NA⁺) |
| P11* (1.00) | H | CH₂ | CH₂ | CH₂ | C | C | H | B | 0.90 | 302, (M + H⁺) |

*in 1/1 mixture of diastreoisomers with the corresponding compound B.

TABLE B

Compounds of Formula (I), more polar diastereoisomer
(R2 = R3 = R4 = R5 = R8 = H, A4 = CH$_2$, R6 = Me, W = O)

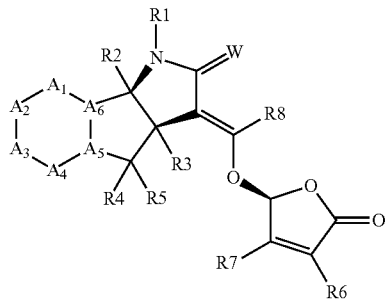

| Ex. | R1 | A$_1$ | A$_2$ | A$_3$ | A$_5$ | A$_6$ | R$_7$ | LCMS | Retention | Mass |
|---|---|---|---|---|---|---|---|---|---|---|
| B1 | H | C(CH$_3$)$_2$ | CH$_2$ | CH$_2$ | C | C | H | B | 0.94 | 330 (M + H$^+$) |
| B2 | H | CH | CH$_2$ | CH$_2$ | CH | C | H | B | 0.89 | 302 (M + H$^+$) |
| B3 | Boc | CH | CH$_2$ | CH$_2$ | CH | C | H | B | 1.14 | 402 (M + H$^+$) |
| B4* | H | CH | | CH$_2$ | CH | C | H | C | 0.85 | 288 (M + H$^+$) |
| B5* | Boc | CH | | CH$_2$ | CH | C | H | C | 1.09 | 797 (2M + Na$^+$) |
| B6* | Ac | CH | | CH$_2$ | CH | C | H | C | 0.97 | 330 (M + H$^+$) |
| B7* | Boc | CH$_2$ | | CH$_2$ | CH | CH | H | B | 1.12 | 390 (M + H$^+$) |
| B8* | H | CH$_2$ | | CH$_2$ | CH | CH | H | B | 0.85 | 290 (M + H$^+$) |
| B9* | H | C(CH$_3$)$_2$ | CH$_2$ | CH$_2$ | C | C | Me | C | 0.75 | 344 (M + H$^+$) |
| B10* | Boc | CH$_2$ | CH$_2$ | CH$_2$ | C | C | H | B | 1.15 | 465 (M + MeCN + Na$^+$) |
| B11* | H | CH$_2$ | CH$_2$ | CH$_2$ | C | C | H | C | 0.90 | 302 (M + H$^+$) |

*in 1/1 mixture of diastreoisomers with the corresponding compound A.

TABLE C

Compounds of Formula (IIb)
(R2 = R3 = R4 = R5 = R8 = H, A$_4$ = CH$_2$, W = O)

(II)

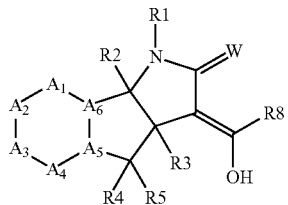

| Ex. | R1 | A$_1$ | A$_2$ | A$_3$ | A$_5$ | A$_6$ | LCMS method | Retention (min.) | Mass |
|---|---|---|---|---|---|---|---|---|---|
| C1 (2.02) | H | C(CH$_3$)$_2$ | CH$_2$ | CH$_2$ | C | C | A | 1.52 | 232 (M − H+) |
| C2 | Boc | CH | CH$_2$ | CH$_2$ | CH | C | C | 1.04 | 328 (M + Na$^+$) |
| C3 | Boc | CH | CH$_2$ | | CH | C | C | 0.99 | 314 (M + Na$^+$) |
| C4 | Boc | CH$_2$ | CH$_2$ | | CH | CH | B | 1.02 | 292 (M − H$^+$) |
| C5 | Boc | CH$_2$ | CH$_2$ | CH$_2$ | C | C | B | 1.06 | 328 (M + Na$^+$) |

Biological Examples

The effect of compounds of Formula (I) on germination of *Orobanche cumana* Wallr. seeds was evaluated on glass fiber filter paper (GFFP) in petri dishes. Seeds were preconditioned at moisture and suitable temperature to become responsive to the specific chemical germination stimulants.

Test compounds were dissolved in DMSO (10 000 mg l$^{-1}$) and stored at room temperature in a desiccators with desiccants. The stock solutions were dissolved with deionised water to the appropriate final test concentration.

Seeds of *O. cumana* race 'F' were collected from a sunflower field in Manzanilla (Seville, Spain) in 2006 (IN146) and 2008 (IN153), respectively and stored at room temperature. To separate seeds from heavy organic debris, a modified sucrose floatation technique as described by Hartman & Tanimonure (Plant Disease (1991), 75, p. 494) was applied. Seeds were filled into a separation funnel and stirred in water. When seeds floated to the surface, the water fraction containing heavy debris was discarded. Seeds were re-suspended in 2.5M sucrose solution (specific gravity of 1.20) and heavy debris was allowed to settle down for 60 min. After removing debris, seeds were disinfected in 1% sodium hypochlorite solution and 0.025% (v/v) Tween 20 for 2 min. The seeds were decanted onto two layers of cheesecloth, rinsed with sterile deionised water and re-suspended in sterile deionised water. Two ml of the seed suspension containing approximately 150-400 seeds were spread evenly on two layers of sterile glass fiber filter paper disc (Ø9 mm) in Petri dishes (Ø9 cm). After wetting the discs with 3 ml sterile deionised water, petri dishes were sealed with parafilm. Seeds were incubated for 10 days at 20° C. in the dark for seed conditioning. The upper disc with conditioned seeds was briefly dried, transferred to a petri dish lined with a dry GFFP disc, and wetted with 6 ml of the appropriate test solution. The compounds of formula (I) were tested at concentrations of 0.001, 0.01, and 0.1 mg $l^{-1}$. The strigolactone analogue GR24 was included as positive control and 0.001% DMSO as negative control. All treatments were tested in five replicates. Seeds were re-incubated at 20° C. in the dark and examined for germination 10 days later. The radicles of germinated seeds were stained for 5 min with blue ink (MIGROS, Switzerland) in 5% acetic acid according to Long et al. Seed Science Research (2008), 18, p. 125). After staining, seeds were photographed using a camera stand mounted with a digital SLR camera (Canon EOS 5D). Germination of 100 seeds per replicate was evaluated on digital images. Seeds were considered germinated when the radicle protruded from the seed coat. The results of the *Orobanche* seed germination tests are shown in Tables 3 to 6.

TABLE 3

Effect of strigolactone analogs on germination of preconditioned *Orobanche cumana* seeds.

| Compound | Concentration (mg $l^{-1}$) | Germination (%)* |
|---|---|---|
| None (Control, 0.001% DMSO) | 0 | 0.2 |
| P1 | 0.001 | 88 |
|  | 0.01 | 88 |
|  | 0.1 | 88.4 |
| GR24 | 0.001 | 20.4 |
|  | 0.01 | 61.0 |
|  | 0.1 | 86.2 |

*Mean; N = 5 × 100 seeds; Seed lot IN146

TABLE 4

Effect of strigolactone analogs on germination of preconditioned *Orobanche cumana* seeds.

| Compound | Concentration (mg $l^{-1}$) | Germination (%)* |
|---|---|---|
| None (Control, 0.001% DMSO) | 0 | 1.4 |
| P2 | 0.001 | 92.6 |
|  | 0.01 | 91.0 |
|  | 0.1 | 91.0 |
| GR24 | 0.001 | 67 |
|  | 0.01 | 65 |
|  | 0.1 | 78.4 |

*Mean; N = 5 × 100 seeds; Seed lot IN153

TABLE 5

Effect of strigolactone analogs on germination of preconditioned *Orobanche cumana* seeds.

| Compound | Concentration (mg $l^{-1}$) | Germination (%)* |
|---|---|---|
| None (Control, 0.001% DMSO) | 0 | 0.75 |
| B2 | 0.01 | 80.4 |
|  | 0.1 | 89.2 |
|  | 1.0 | 91.8 |
| GR24 | 0.001 | 88 |
|  | 0.01 | 86.6 |
|  | 0.1 | 95.2 |

*Mean; N = 5 × 100 seeds; Seed lot IN153

TABLE 6

Effect of strigolactone analogs on germination of preconditioned *Orobanche cumana* seeds.

| Compound | Concentration (mg $l^{-1}$) | Germination (%)* |
|---|---|---|
| None (Control, 0.001% DMSO) | 0 | 0 |
| P4 | 0.001 | 73.4 |
|  | 0.01 | 82.6 |
|  | 0.1 | 68.4 |
| P5 | 0.001 | 90.6 |
|  | 0.01 | 80.8 |
|  | 0.1 | 89.6 |
| GR24 | 0.001 | 26 |
|  | 0.01 | 51 |
|  | 0.1 | 84.2 |

*Mean; N = 5 × 100 seeds; Seed lot IN153

The results show that compound P1, P2, B2, P4, and P5 results in a germination inducing effect.

Biological Examples

The effect of compounds of Formula (I) on the germination of *Brassica oleracea* cv *Botrytis* or common cauliflower was tested on two types of cauliflowers: temperate types and tropical types. These two types were chosen because they display different sensitivities to the light conditions and temperature during germination. Germination of a sensitive temperate type is inhibited by light at 10° C. while for the tropical types germination at 20° is stimulated by the presence of light. Hence, 10° C. in the light and 20° C. in the dark are considered suboptimal or stress conditions for germination of the two types, respectively.

The temperate seed batches tested are part of commercially produced seed batches of various varieties which are known to be sensitive to light at 10° C. These seeds were harvested and cleaned according standard commercial procedures. Ready seed batches were used (Ready indicates the processing level of these seeds: they have been cleaned and sized but received no other treatments). The tropical seed batches tested are part of seed batches produced as basic seed (for maintenance of the parental line) and were processed accordingly.

Germination was assessed using the standard paper germination test for *Brassica*: Fifty seeds were placed on blue germination paper, which was moistened with the appropriate solutions, in closed oblong germination boxes. Each condition was tested in duplo. Germination boxes were placed in controlled germination cabinets with the appropriate temperature and light conditions. Germination of seeds was counted at regular intervals. Seeds were considered to be germinated when the radical had protruded the testa and endosperm (radical size approximately 1 mm). Germination kinetics were analyzed using the Germinator analysis tool in order to obtain the parameters: $G_{max}$ (maximum germination) and $t_{50}$ (time needed to reach 50% of the $G_{max}$). The Germinator analysis tool is an add-in in for excel developed by the University of Wageningen: Joosen, R. V. L., J. Kodde, et al. (2010). ("Germinator: A Software Package for High-Throughput Scoring and Curve Fitting of *Arabidopsis* Seed Germination." The Plant Journal 62(1): 148-159.)

Test compounds were dissolved in DMSO at a concentration of 50 mM and stored at −20° C. The strigolactone analogue GR24 (commercially available as a racemic mixture of 2 diastereoisomers, referred to as "synthetic strigolactone GR-24" and first prepared by Johnson A. W. & all, Journal of the Chemical Society, Perkin Transactions 1, 1981, page 1734-1743) was included as positive control. Germination solutions were prepared by diluting the stock solutions with demineralized water till 25 µM. As control solutions demineralized water and a 0.05% v/v DMSO solution were used.

The effect of the strigolactone derivatives on germination is shown in tables 7 and 8. These results show that strigolactones stimulate germination at suboptimal conditions.

TABLE 7

Germination of seeds of the tropical cauliflower 3C150 (seed batch 11B295; produced in Chili 2011) in the presence of 25 µM of the different strigolactone derivatives at 20° C. and in the dark.

| compound | $G_{max}{}^a$ (%) | stimulation[b] (%) |
|---|---|---|
| DMSO | 31.3 | 0.0 |
| GR24 | 73.0 | 140.0 |
| P1 | 55.0 | 80.0 |

[a]total germination.
[b]extra germination compared to the DMSO treatment, expressed as percentage of the DMSO treatment.

TABLE 8

Germination of seeds of the tropical cauliflower 3C150 (seed batch 11B552; produced in South Africa 2010) in the presence of 25 µM of the different strigolactone derivatives at 20° C. and in the dark.

| compound | $G_{max}{}^a$ (%) | $t_{50}{}^b$ (h) | acceleration[c] (h) |
|---|---|---|---|
| DMSO | 96.7 | 80.9 | 0.0 |
| GR24 | 100.0 | 72.2 | 8.7 |
| P1 | 95.0 | 74.3 | 6.6 |

[a]total germination.
[b]time needed to reach 50% of total germination
[c]hours faster than the DMSO treatment to reach 50% of total germination

The invention claimed is:
1. A compound of Formula (I)

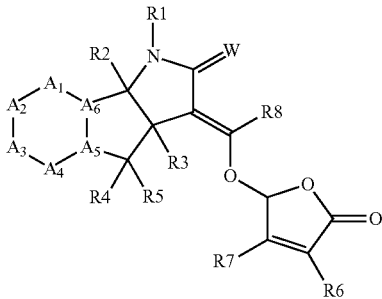

(I)

wherein
W is O or S;
R2 and R3 are independently hydrogen, or $C_1$-$C_3$ alkyl;
R4 and R5 are independently hydrogen, halogen, nitro, cyano, $C_1$-$C_3$ alkyl, $C_1$-$C_3$ haloalkyl, $C_1$-$C_3$ alkoxy, hydroxyl, —OC(O)R9, amine, N—$C_1$-$C_3$ alkyl amine, or N,N-di-$C_1$-$C_3$ alkyl amine;
R9 is hydrogen, $C_1$-$C_6$ alkyl, $C_1$-$C_6$ alkoxy, or $C_1$-$C_6$ haloalkyl;
R6 and R7 are independently hydrogen, $C_1$-$C_3$ alkyl, hydroxyl, halogen or $C_1$-$C_3$ alkoxy;
R8 is hydrogen, nitro, cyano, $C_1$-$C_6$ alkyl, $C_1$-$C_6$ haloalkyl, halogen, $C_1$-$C_8$ alkylthio, $C_1$-$C_8$ haloalkylthio, $C_1$-$C_8$ alkylsulfinyl, N—$C_1$-$C_6$ alkyl amine, N,N-di-$C_1$-$C_6$ alkyl amine, $C_1$-$C_8$ haloalkylsulfinyl, $C_1$-$C_8$ alkylsulfonyl, or $C_1$-$C_8$ haloalkylsulfonyl;
R1 is hydrogen, $C_1$-$C_6$ alkoxy, hydroxyl, amine, N—$C_1$-$C_6$ alkyl amine, N,N-di-$C_1$-$C_6$ alkyl amine, $C_1$-$C_6$ alkyl optionally substituted by one to five R10, $C_1$-$C_8$ alkylcarbonyl, $C_1$-$C_8$ alkoxycarbonyl, aryl, optionally substituted by one to five R10, heteroaryl, optionally substituted by one to five R10, heterocyclyl, optionally substituted by one to five R10, or benzyl optionally substituted by one to five R10;
R10 is hydrogen, cyano, nitro, halogen, $C_1$-$C_6$ alkyl, $C_1$-$C_6$ alkoxy, $C_1$-$C_6$ haloalkyl, $C_2$-$C_6$ alkenyl, or $C_2$-$C_6$ alkynyl;
$A_1$, $A_2$, and $A_3$ are each independently C-Xn, C-(Xn)C-(Xn), a heteroatom selected from O, S and N, wherein each X may be the same or different, or a bond;
$A_4$ is C-Xn, or a heteroatom selected from O, S and N, wherein each X may be the same or different;
$A_5$, and $A_6$ are each independently C-X, nitrogen, or C linked by a double bond, wherein each X may be the same or different;
$A_1$ and $A_2$, $A_2$ and $A_3$, $A_3$ and $A_4$, $A_4$ and $A_5$, $A_5$ and $A_6$, $A_6$ and $A_1$ are linked independently of each other by a single or double bond provided that $A_1$ to $A_6$ is not an aromatic ring;
n is 1 or 2;
X is hydrogen, halogen, cyano, amine, nitro, hydroxyl, —OC(O)R9, $C_1$-$C_6$ alkoxy, $C_1$-$C_6$ alkyl, $C_1$-$C_6$ haloalkyl, $C_1$-$C_6$ hydroxyalkyl; $C_2$-$C_5$ alkenyl optionally substituted by one to five R11, $C_2$-$C_5$ alkynyl optionally substituted by one to five R11, $C_3$-$C_7$ cycloalkyl, $C_3$-$C_{10}$ cycloalkyl substituted by one to five R11, $C_1$-$C_5$alkylcarbonyl, $C_1$-$C_8$ alkoxycarbonyl, N—$C_1$-$C_6$ alkyl aminocarbonyl, N,N-di-$C_1$-$C_6$ alkyl aminocarbonyl, aryl optionally substituted by one to five R11, or heterocyclic optionally substituted by one to five R11; and
R11 is halogen, nitro, cyano, hydroxyl, —OC(O)R9, $C_1$-$C_6$ alkoxy, $C_1$-$C_6$ alkyl, $C_1$-$C_6$ haloalkyl;
or salts or N-oxides thereof.
2. A compound according to claim 1, wherein W is O.
3. A compound according to claim 1, wherein:
R2 and R3 are independently hydrogen, methyl, or ethyl;
R4 and R5 are independently hydrogen, hydroxyl, methyl or ethyl;
R6, R7 and R8 are independently hydrogen, methyl or ethyl;
R1 is hydrogen, $C_1$-$C_6$ alkoxy, $C_1$-$C_6$ alkyl optionally substituted by one to five R10, $C_1$-$C_8$ alkylcarbonyl, $C_1$-$C_8$ alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10; and
R10 is independently hydrogen, cyano, nitro, halogen, $C_1$-$C_6$ alkyl, $C_1$-$C_6$ alkoxy, $C_1$-$C_6$ haloalkyl;
$A_1$, $A_2$, $A_3$ and $A_4$ are C-Xn;
$A_5$ and $A_6$ are independently C-X, or C linked by a double bond;
n is 1 or 2; and
X is hydrogen, methyl, ethyl, fluoro, hydroxyl, methylhydroxyl, methoxy, or methylacetate.
4. A compound according to claim 1, wherein $A_5$ and $A_6$ are C linked by a double bond.

5. A plant growth regulator or seed germination promoting composition, comprising a compound according to claim 1, and an agriculturally acceptable formulation adjuvant.

6. A method for regulating the growth of plants at a locus, wherein the method comprises applying to the locus a plant growth regulating amount of the compound according to claim 1.

7. A method for promoting the germination of seeds comprising applying to the seeds, or a locus containing seeds, a seed germination promoting amount of the compound according to claim 1.

8. The method according to claim 7 wherein the plant of the seed is a plant selected from the genus *brassica*.

9. A method for controlling weeds comprising applying to a locus containing weed seeds a seed germination promoting amount of the compound according to claim 1, allowing the seeds to germinate, and then applying to the locus a post-emergence herbicide.

10. A compound of Formula (II)

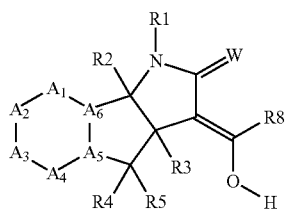

(II)

wherein
W is O or S;
R2 and R3 are independently hydrogen, or $C_1$-$C_3$ alkyl;
R4 and R5 are independently hydrogen, halogen, nitro, cyano, $C_1$-$C_3$ alkyl, $C_1$-$C_3$ haloalkyl, $C_1$-$C_3$ alkoxy, hydroxyl, —OC(O)R9, amine, N—$C_1$-$C_3$ alkyl amine, or N,N-di-$C_1$-$C_3$ alkyl amine;
R9 is hydrogen, $C_1$-$C_6$ alkyl, $C_1$-$C_6$ alkoxy, or $C_1$-$C_6$ haloalkyl;
R8 is hydrogen, nitro, cyano, $C_1$-$C_6$ alkyl, $C_1$-$C_6$ haloalkyl, halogen, $C_1$-$C_8$ alkylthio, $C_1$-$C_5$ haloalkylthio, $C_1$-$C_5$ alkylsulfinyl, N—$C_1$-$C_6$ alkyl amine, N,N-di-$C_1$-$C_6$ alkyl amine, $C_1$-$C_8$ haloalkylsulfinyl, $C_1$-$C_8$ alkylsulfonyl, or $C_1$-$C_8$ haloalkylsulfonyl;
R1 is hydrogen, $C_1$-$C_6$ alkoxy, amine, N—$C_1$-$C_6$ alkyl amine, N,N-di-$C_1$-$C_6$ alkyl amine, $C_1$-$C_6$ alkyl optionally substituted by one to five R10, $C_1$-$C_8$ alkylcarbonyl, $C_1$-$C_5$ alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;
R10 is hydrogen, cyano, nitro, halogen, $C_1$-$C_6$ alkyl, $C_1$-$C_6$ alkoxy, $C_1$-$C_6$ haloalkyl, $C_2$-$C_6$ alkenyl, or $C_2$-$C_6$ alkynyl;
$A_1$, $A_2$, and $A_3$ are each independently C-Xn, C-(Xn)C-(Xn), a heteroatom selected from O, S and N, wherein each X may be the same or different, or a bond;
$A_4$ is C-Xn, or a heteroatom selected from O, S and N, wherein each X may be the same or different;
$A_5$, and $A_6$ are each independently C-X, nitrogen, or C linked by a double bond, wherein each X may be the same or different;
$A_1$ and $A_2$, $A_2$ and $A_3$, $A_3$ and $A_4$, $A_4$ and $A_5$, $A_5$ and $A_6$, $A_6$ and $A_1$ are linked independently of each other by a single or double bond provided that $A_1$ to $A_6$ is not an aromatic ring;
n is 1 or 2;
X is hydrogen, halogen, cyano, amine, nitro, hydroxyl, —OC(O)R9, $C_1$-$C_6$ alkoxy, $C_1$-$C_6$ alkyl, $C_1$-$C_6$ haloalkyl, $C_1$-$C_6$ hydroxyalkyl; $C_2$-$C_5$ alkenyl optionally substituted by one to five R11, $C_2$-$C_5$ alkynyl optionally substituted by one to five R11, $C_3$-$C_7$ cycloalkyl, $C_3$-$C_{10}$ cycloalkyl substituted by one to five R11, $C_1$-$C_8$alkylcarbonyl, $C_1$-$C_8$ alkoxycarbonyl, N—$C_1$-$C_6$ alkyl aminocarbonyl, N,N-di-$C_1$-$C_6$ alkyl aminocarbonyl, aryl optionally substituted by one to five R11, or heterocyclic optionally substituted by one to five R11; and
R11 is halogen, nitro, cyano, hydroxyl, —OC(O)R9, $C_1$-$C_6$ alkoxy, $C_1$-$C_6$ alkyl, $C_1$-$C_6$ haloalkyl;
or salts or N-oxides thereof.

11. A method of enhancing crop plants by applying to the plants, plant parts, plant propagation material, or a plant growing locus, a compound according to claim 1.

12. A method according to claim 11 for improving plant yield, comprising applying to a plant, plant part, plant propagation material, or a plant growing locus, a compound according to claim 1.

13. A method according to claim 11 for improving plant input use efficiency, comprising applying to a plant, plant part, plant propagation material, or a plant growing locus, a compound according to claim 1.

14. A method according to claim 11 for improving plant vigour and/or plant quality, and/or plant tolerance to stress factors, comprising applying to a plant, plant part, plant propagation material, or a plant growing locus, a compound according to claim 1.

15. A compound according to claim 1, wherein
W is O;
R1, R2, R3, R4, R5, R7 and R8 are H;
R6 is methyl;
$A_1$, $A_2$, $A_3$ and $A_4$ are C-Xn;
$A_5$ and $A_6$ are independently C-X, or C linked by a double bond;
n is 1 or 2; and
X is hydrogen, methyl, ethyl, fluoro, hydroxyl, methylhydroxyl, methoxy, or methylacetate.

16. A compound according to claim 1, wherein
W is O;
R1, R2, R3, R4, R5, R7 and R8 are H;
R6 is methyl;
$A_1$ is $C(CH_3)_2$;
$A_2$, $A_3$ and $A_4$ are $CH_2$; and
$A_5$ and $A_6$ are C linked by a double bond.

* * * * *